US008494229B2

(12) United States Patent
Järvenpää et al.

(10) Patent No.: US 8,494,229 B2
(45) Date of Patent: Jul. 23, 2013

(54) DEVICE AND METHOD FOR DETERMINING GAZE DIRECTION

(75) Inventors: Toni Järvenpää, Toijala (FI); Tapani Levola, Tampere (FI)

(73) Assignee: Nokia Corporation, Espoo (FI)

( * ) Notice: Subject to any disclaimer, the term of this patent is extended or adjusted under 35 U.S.C. 154(b) by 357 days.

(21) Appl. No.: 12/866,427

(22) PCT Filed: Feb. 14, 2008

(86) PCT No.: PCT/FI2008/050065
§ 371 (c)(1),
(2), (4) Date: Sep. 22, 2010

(87) PCT Pub. No.: WO2009/101238
PCT Pub. Date: Aug. 20, 2009

(65) Prior Publication Data
US 2011/0019874 A1    Jan. 27, 2011

(51) Int. Cl.
*G06K 9/00* (2006.01)
*A61B 3/10* (2006.01)
(52) U.S. Cl.
USPC ............ 382/117; 382/103; 351/206; 351/221
(58) Field of Classification Search
USPC ........................... 382/103, 117; 351/206, 221
See application file for complete search history.

(56) References Cited

U.S. PATENT DOCUMENTS

| 5,861,940 | A * | 1/1999 | Robinson et al. | 351/221 |
| 6,152,563 | A * | 11/2000 | Hutchinson et al. | 351/209 |
| 6,161,932 | A * | 12/2000 | Goto et al. | 351/208 |
| 7,572,008 | B2 * | 8/2009 | Elvesjo et al. | 351/206 |
| 2002/0051116 | A1 * | 5/2002 | Van Saarloos et al. | 351/204 |
| 2006/0126181 | A1 * | 6/2006 | Levola | 359/567 |
| 2006/0238707 | A1 * | 10/2006 | Elvesjo et al. | 351/209 |
| 2011/0109880 | A1 * | 5/2011 | Nummela | 351/210 |

FOREIGN PATENT DOCUMENTS

| EP | 0 821 908 | 2/1998 |
| EP | 0 942 350 | 2/2003 |
| WO | WO0027273 | 5/2000 |
| WO | WO 2004045399 | 6/2004 |
| WO | WO 2007085682 | 8/2007 |

OTHER PUBLICATIONS

International Search Report of PCT/FI2008/050065—Date of Completion of Search: Oct. 21, 2008.
Supplementary European Search Report for European Application No. EP08718518—Date of Completion of Search: Jan. 31, 2013, 5 pages.

* cited by examiner

*Primary Examiner* — Stephen R Koziol
*Assistant Examiner* — Delomia Gilliard
(74) *Attorney, Agent, or Firm* — Locke Lord LLP

(57) ABSTRACT

An eye tracker device (200) comprises a diffractive beam expander (207) to provide two substantially collimated illuminating light beams (B11, B12). The collimated light beams (B11, B12) provide two reflection spots (G1, G2) appearing in the image of the eye. The gaze direction (GZD) is calculated from the positions of the reflection spots (G1, G2) with respect to the pupil (P) of the eye (E1). The two illuminating beams (B11, B12) are provided by splitting an infrared laser beam (B4) into two in-coupled beams (B5, B6), which propagate in different directions in the substrate (7) of the beams expander. The in-coupled beams (B5, B6) are expanded and their light is subsequently coupled out of the substrate (7) by an out-coupling grating (230) to illuminate the eye (E1). The same substrate (7) may also be used to implement a virtual display device (100) for displaying virtual images to said eye (E1).

20 Claims, 23 Drawing Sheets

DEVICE AND METHOD FOR DETERMINING GAZE DIRECTION

The present invention relates to the determination of the gaze direction of an eye.

BACKGROUND

The gaze direction of a person may be used to select options displayed on a computer screen. Thus, an eye tracker device providing information on the gaze direction may be used, for example, as a pointing and selecting device instead of a computer mouse.

When light impinges on the eye, several reflections occur on the boundaries of the lens, cornea and retina. These reflections provide reflection spots known as the Purkinje images. The reflection from the outer corneal surface provides the first Purkinje image, also called as the glint. The orientation of the eye may be determined based on the position of the pupil with respect to the position of the first Purkinje image.

Patent application PCT/FI2006/050043 discloses an eye tracker device comprising a diffractive beam expander to provide two illuminating beams. The use of two Purkinje images makes the determination substantially independent of the distance between the eye and the tracker device. Said application discloses also that the eye tracker device may be used in combination with a virtual display unit, wherein said virtual display unit is arranged to display virtual images.

SUMMARY

An object of the present invention is to provide a device and a method for determining the gaze direction.

According to a first aspect of the invention, there is provided a device for determining the gaze direction of an eye, said device comprising:
- a first imaging unit to acquire an image of said eye,
- a substantially planar waveguiding substrate,
- a light source to provide a first light beam, said first light beam being substantially collimated,
- an in-coupling grating to diffract light of said light beam into said substrate and to form a first in-coupled beam and a second in-coupled beam propagating in different directions within said substrate,
- a first expanding grating portion to provide a first expanded internal beam by diffracting light of said first in-coupled beam,
- a second expanding grating portion to provide a second expanded internal beam by diffracting light of said second in-coupled beam,
- a first out-coupling grating portion to form a first substantially collimated illuminating beam by diffracting light of said first internal beam out of said substrate,
- a second out-coupling grating portion to form a second substantially collimated illuminating beam by diffracting light of said second internal beam out of said substrate, said illuminating beams having different directions with respect to said device such that said first illuminating beam provides a first reflection spot when light is reflected from the surface of the eye and that said second illuminating beam provides a second reflection spot when light is reflected from the surface of said eye, said reflection spots appearing in said image, and
- a data processing unit to determine the gaze direction of the eye with respect to said device based on the position of said first reflection spot in said image, on the position of said second reflection spot in said image, on the position of the pupil and/or iris of the eye in said image, and on the directions of the illuminating light beams.

According to a second aspect of the invention, there is provided a method for determining the gaze direction of an eye, said method comprising:
- acquiring an image of said eye by using a first imaging unit,
- providing a substantially collimated first light beam by using a light source,
- diffracting light of said first light beam by using an in-coupling grating in order to form a first in-coupled beam and a second in-coupled beam propagating in different directions within a substantially planar waveguiding substrate,
- diffracting light of said first in-coupled beam by a first expanding grating portion to provide a first expanded internal beam propagating within said substrate,
- diffracting light of said second in-coupled beam by a second expanding grating portion to provide a second expanded internal beam propagating within said substrate,
- diffracting light of said first expanded internal beam by a first out-coupling grating portion out of said substrate to form a first substantially collimated illuminating beam,
- diffracting light of said second expanded internal beam out of said substrate to form a second substantially collimated illuminating beam, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image, and
- determining the gaze direction of the eye based on the position of said first reflection spot in said image, on the position of said second reflection spot in said image, on the position of the pupil and/or iris of the eye in said image and on the directions of the illuminating light beams.

According to a third aspect of the invention there is provided a portable device for displaying virtual images and for determining the gaze direction of an eye, said device comprising:
- a first imaging unit to acquire an image of said eye,
- a substantially planar waveguiding substrate,
- a light source to provide a first light beam, said first light beam being substantially collimated,
- an in-coupling grating to diffract light of said light beam into said substrate and to form a first in-coupled beam and a second in-coupled beam propagating in different directions within said substrate,
- a first expanding grating portion to provide a first expanded internal beam by diffracting light of said first in-coupled beam,
- a second expanding grating portion to provide a second expanded internal beam by diffracting light of said second in-coupled beam,
- a first out-coupling grating portion to form a first substantially collimated illuminating beam by diffracting light of said first internal beam out of said substrate,
- a second out-coupling grating portion to form a second substantially collimated illuminating beam by diffracting light of said second internal beam out of said substrate, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image, a data processing unit to determine the gaze direction of the eye with respect to said device based on the position of said first reflection spot in said image, on the position of said second reflection spot in said image, on the position of the pupil and/or iris of the eye in said image and on the directions of the illuminating light beams.

an optical engine to provide at least one light beam, and a diffractive beam expander to expand said at least one light beam such that a virtual image is visually observable through a viewing aperture of said diffractive beam expander.

According to a fourth aspect of the invention, there is provided a gaze direction determining means for determining the gaze direction of an eye, said means comprising:

a first imaging means to acquire an image of said eye, a substantially planar waveguiding substrate, a light source means to provide a first light beam, said first light beam being substantially collimated, an in-coupling grating to diffract light of said light beam into said substrate and to form a first in-coupled beam and a second in-coupled beam propagating in different directions within said substrate, a first expanding grating portion to provide a first expanded internal beam by diffracting light of said first in-coupled beam, a second expanding grating portion to provide a second expanded internal beam by diffracting light of said second in-coupled beam, a first out-coupling grating portion to form a first substantially collimated illuminating beam by diffracting light of said first internal beam out of said substrate, a second out-coupling grating portion to form a second substantially collimated illuminating beam by diffracting light of said second internal beam out of said substrate, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image, and a data processing means to determine the gaze direction of the eye with respect to said gaze direction determining means based on the position of said first reflection spot in said image, on the position of said second reflection spot in said image, on the position of the pupil and/or iris of the eye in said image, and on the directions of the illuminating light beams.

The splitting of a single collimated beam by the in-coupling grating into at least two parts provides a simple and stable way to arrange the illumination of the eye.

In an embodiment, the device comprises also an optical engine and a further diffractive beam expander to display virtual images. The same out-coupling grating may be used for providing the illuminating beams and an virtual image.

In an embodiment, the device comprises also an optical engine and a further diffractive beam expander to display virtual images. The first diffractive beam expander of the eye tracker unit and the second diffractive beam expander for displaying virtual images may be implemented on the same substrate. The diffractive features of the output grating of the first diffractive beam expander may be substantially perpendicular to the diffractive features of the out-coupling grating of the second diffractive beam expander. Consequently, only minimum amount of illuminating light is coupled out of the substrate by the output grating of the second diffractive beam expander and/or the illuminating light coupled out of the substrate by the output grating of the second diffractive beam expander propagate in directions which do not disturb the determination of the gaze direction.

BRIEF DESCRIPTION OF THE DRAWINGS

In the following examples, the embodiments of the invention will be described in more detail with reference to the appended drawings, in which.

DETAILED DESCRIPTION

Figure 1A:
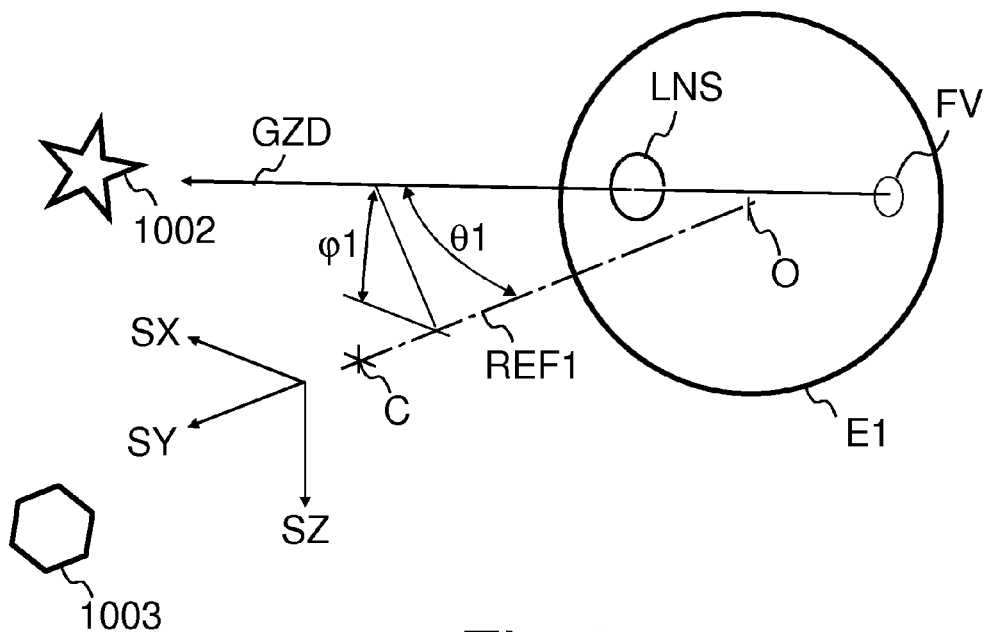
FIG. 1a shows, in a three dimensional view, the gaze direction of an eye with respect to a reference coordinate system.

Referring to FIG. 1a, the gaze direction GZD of the eye E1 may be expressed by the zenith angle $\theta 1$ and the azimuth angle $\phi 1$ of the gaze direction GZD with respect to the directions SX, SY, and SZ of a reference coordinate system. The direction SZ defines the vertical direction and the direction SX defines the horizontal direction of the reference coordinate system. The directions SX, SY, and SZ are orthogonal. See FIG. 11a for the definition of the zenith and azimuth angles.

A portion of the retina of the eye E1, called as the fovea FV, is responsible for the most sharp vision. The gaze direction GZD may be defined by a line passing through the center of the fovea FV and the principal point of the lens LNS of the eye E1.

A reference line REF1 is parallel to the direction SY of the reference coordinate system. The position of the eye E1 may be moved in the directions SX, SY, and/or SZ.

The reference line REF1 does not, in general, pass through the center O of the eye E1.

Objects 1002, 1003 are located at a considerable or infinite distance from the eye E1. The objects 1002, 1003 may be physical objects (e.g. bodies), images displayed on a remote display screen, or images displayed by a virtual display.

It is assumed that the angular coordinates of the objects 1002, 1003 are known with respect to a point C on the reference line REF1, and that the distance between the eye E1 and the objects 1002, 1003 is long when compared to the distance between the point C and the eye center O. The ratio of the distances may be e.g. greater than or equal to ten. Thus, the objects 1002, 1003 may be associated with gaze directions GZD. Consequently, by knowing the zenith angle $\theta 1$ and the azimuth angle $\phi 1$ of the gaze direction GZD, it may be determined which object the eye E1 is looking at, e.g. whether the eye E1 is looking at the star 1002 or the hexagon 1003.

Figure 1B:
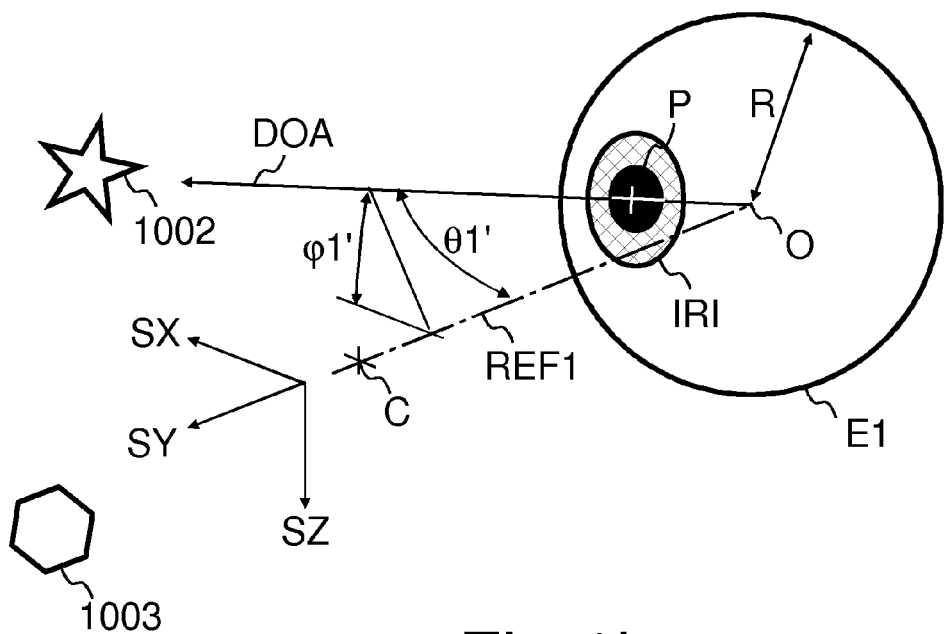
FIG. 1b shows, in a three dimensional view, the direction of the optical axis of the eye with respect to the reference coordinate system of FIG. 1a, FIG. 2 shows, in a side view, an eye tracking device for determining the gaze direction.

Referring to FIG. 1b, the actual form of the eye E1 is slightly non-spherical, but the form of the cornea may be approximated by a spherical surface. Herein, the center O of the eye E1 refers to the center of a best-fit sphere, said sphere being fitted with the corneal surface. Herein, the radius R of the eye E1 refers to the radius of said best-fit sphere.

The direction DOA of the optical axis of the eye E1 is defined by a line passing through the center O of the eye E1 and the best fit center of the pupil P.

The pupil is surrounded by the iris IRI. The determination of the best-fit center of the pupil P may also be determined partly or completely based on the location of the iris IRI.

The gaze direction GZD deviates typically 3-5 degrees from the direction DOA of the optical axis. The relationship between the zenith and azimuth angles $\theta 1'$, $\phi 1'$ of the direction DOA and the zenith and azimuth angles $\theta 1$, $\phi 1$ of the gaze direction GZD may be established by e.g. calibration measurements. Said relationship may be expressed e.g. as regression equations.

Figure 2:
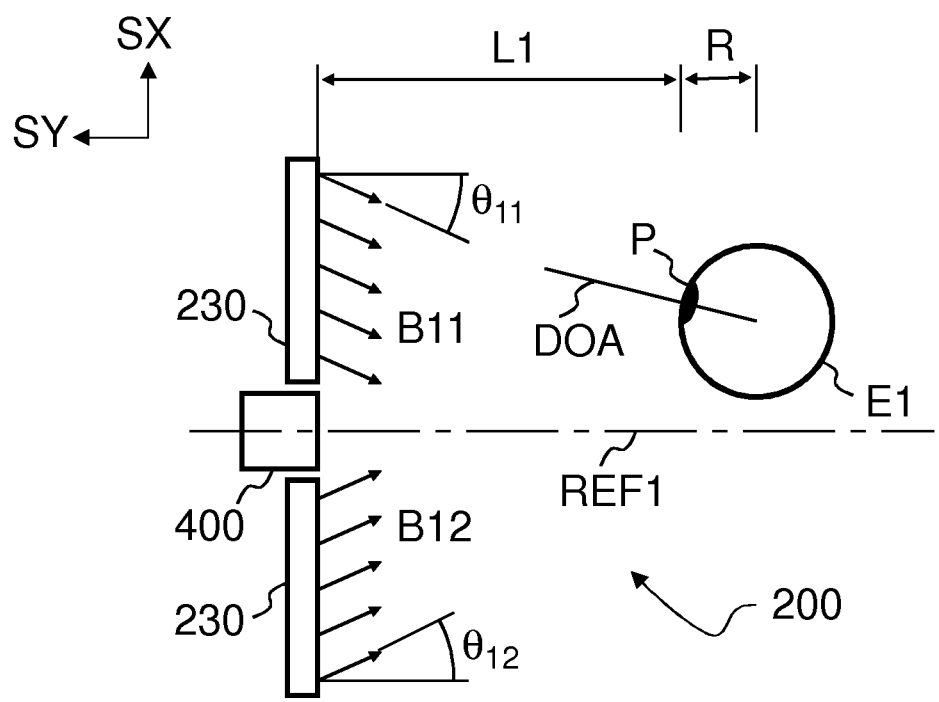

Referring to FIG. 2, the zenith angle $\theta 1'$ and the azimuth angle $\phi 1'$ of the optical axis direction DOA may, in turn, be determined by an eye tracker device 200. The eye tracker device 200 may comprise one or more out-coupling gratings or grating portions 230 and an imaging unit 400. The out-coupling gratings 230 provide at least two substantially collimated light beams B11, B12, which are directed towards the eye E1, and which beams B11, B12 have different directions. The imaging unit 400 provides an image of the eye E1.

The direction of the first illuminating beam B11 may be identified by the zenith angle $\phi_{11}$ and azimuth angle $\theta_{11}$ of said beam B11. The direction of the second illuminating beam B12 may be identified by the zenith angle $\phi_{12}$ and azimuth angle $\theta_{12}$ of said beam B11. Only the zenith angles $\theta_{11}$ and $\theta_{12}$ are shown in FIG. 2. The beams B11 and B12 propagate in different directions, i.e. $\theta_{11} \neq \theta_{12}$ and/or $\phi_{11} \neq \phi_{12}$. L1 denotes the distance between the imaging unit 400 and the pupil P of the eye E1.

The imaging unit 400 comprises imaging optics to focus light onto an image sensor, which may be e.g. a charge coupled device (CCD) or a CMOS image sensor. The imaging unit 400 may comprise means for automatic focusing.

Figure 3:
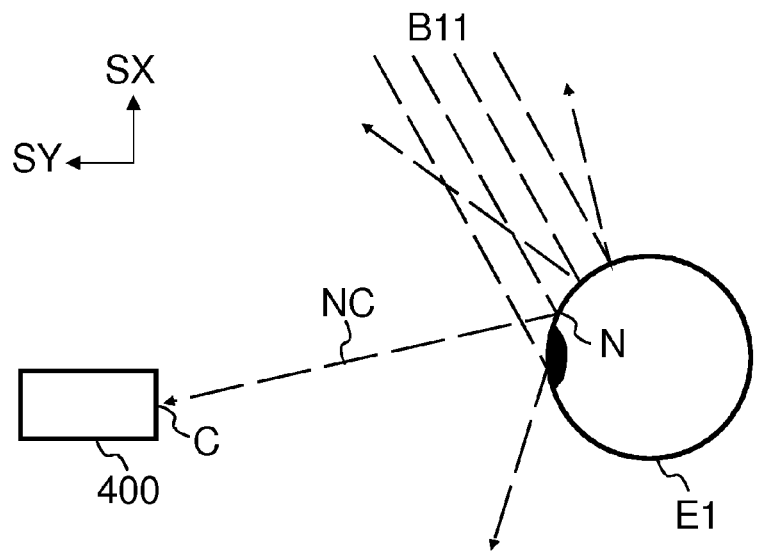
FIG. 3 shows, in a side view, reflection of light rays from the corneal surface.

Referring to FIG. 3, light of the beam B11 is reflected from the corneal surface providing a plurality of reflected rays, which propagate in several different directions. A narrow fan of reflected light rays is received by the aperture of the imaging unit 400. Said fan is herein represented by a single ray NC, which is the weighted average of said fan. The ray NC is reflected from a reflection point N on the surface of the eye E1 to the principal point C of the imaging optics of the imaging unit 400.

Also the second illuminating beam B12 (not shown in FIG. 3) is reflected from the corneal surface towards the imaging unit 400. The second illuminating beam B12 is reflected from a point M (not shown) on the surface of the eye E1 to the principal point C of the imaging optics of the imaging unit 400.

Figure 4:
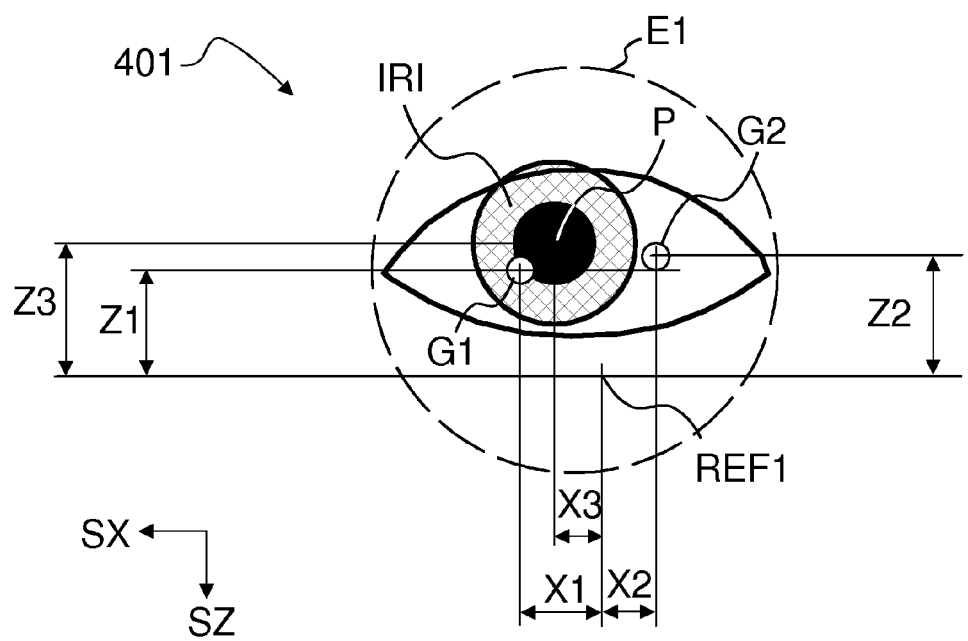
FIG. 4 shows an image of the eye, said image comprising two reflection spots.

FIG. 4 shows an image 401 of the eye E1 as acquired by the imaging unit 400. The first illuminating beam B11 is directed towards the eye E1 such that the reflection of the first beam B11 provides a first reflection spot G1 appearing in the image 401. The second illuminating beam B12 is directed towards the eye E1 such that the reflection of the second beam B12 provides a second reflection spot G2 appearing in the image 401. Image analysis algorithms may be applied to determine the coordinates X1, Z1, X2, Z2 of the reflection spots G1, G2, and the coordinates X3, Z3 of the pupil P in the image 401. The reflection spots G1, G2, i.e. the first Purkinje images should be distinguished from the other Purkinje images originating from the inside of the eye E1.

The pupil refers to the circular transparent zone in the center of the iris IRI. It is the position of this black zone which can be determined by the camera 400 arranged to view the eye E1.

The angular position of the first reflection spot G1 can be defined by a horizontal angle and a vertical angle between the reference direction REF1 and a line drawn from the point C of the imaging optics to the center of the reflection spot G1, i.e. to the point N shown in FIG. 3. The angular positions of the reflection spots G1, G2 and the pupil P can be determined based on the acquired image 401. The relationship between the position of a pixel in the acquired image and the angular position of a feature imaged on said pixel may be calculated based on the known distance between the imaging optics and the image sensor. The relationship may also be determined experimentally in a test bench.

When the gaze direction is changed, the pupil P moves with respect to the reflection spots G1, G2.

The angular difference corresponding to the difference between the positions of the reflection spots G1, G2 establishes a yardstick, which makes the determination of the gaze direction substantially independent of the distance L1 between the imaging optics 400 and the eye E1.

The algorithm for determining the gaze direction GZD and/or the direction DOA of the optical axis, based on the positions of the reflection spots G1, G2 and the pupil P1, has been described e.g. in the patent publication WO2007085682 A1.

The determination of the gaze direction GZD and/or the direction DOA of the optical axis may comprise:
 determining the angular positions of reflection points N, M on the surface of the eye E1 based on coordinates of the reflection spots G1, G2 in the image 401 acquired by the imaging unit 400,
 calculating the directions of surface normals N1, N2 at said reflection points N, M based on the directions of the illuminating beams B11, B12 and the directions of vectors CN and CM drawn from the principal point C of the imaging optics to said points N and M, said surface normals N1, N2 being perpendicular to the surface of the eye E1,
 determining an auxiliary vector GH which is perpendicular to the normals N1 and N2,
 calculating the lengths of vectors GH, CM and CN,
 approximating the position of the eye center O by the mid-point of said auxiliary vector GH,
 determining the direction of a vector CP from the principal point C to the pupil center P based on the coordinates of the pupil P and/or iris in the acquired image 401,
 calculating the position of the pupil center P, and
 calculating the direction of a vector OP from the center O of the eye E1 to the pupil center P, the direction of said vector OP being the direction DOA of the optical axis of the eye E1.

It should be noticed that the pupil and the lens of the eye E1 are not on the surface of the eye E1, but inside the eye E1. The relationship between the gaze direction GZD and the direction DOA of the optical axis established by the above algorithm may be determined by calibration (See the discussion in the context of FIG. 21). Thus, the gaze direction GZD may be determined on the basis of the direction DOA of the optical axis of the eye E1 by using one or more regression equations.

Figure 5A:
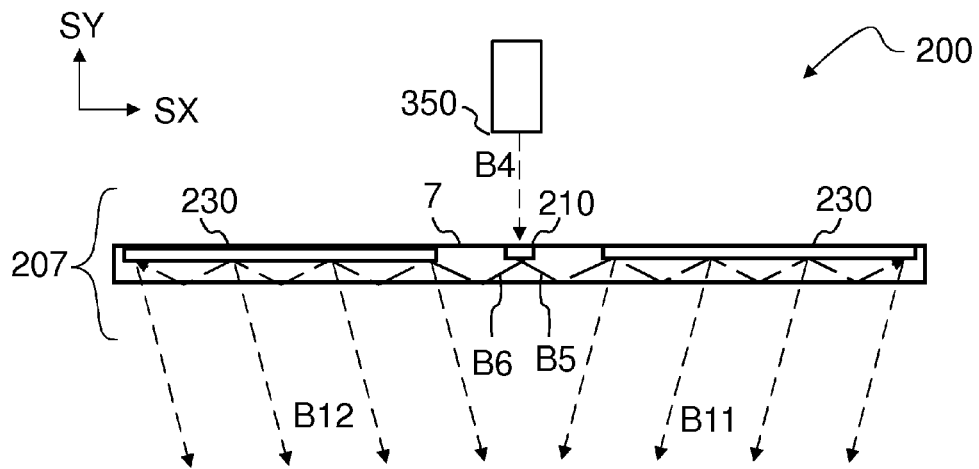
FIG. 5a shows, in a side view, a diffractive beam expander adapted to provide a first collimated illuminating beam and a second collimated illuminating beam.

Referring to FIG. 5a, an eye tracking device 200 may comprise a light source 350 and a diffractive beam expander 207 to provide at least two substantially collimated illuminating beams B11, B12. The eye tracking device 200 comprises also an imaging unit 400 and a data processing unit 550 (see FIG. 17).

The light source 350 may be e.g. a laser which is adapted to emit e.g. infrared light. The imaging unit 400 is sensitive to the wavelength of the light source 350. The imaging unit 400 may comprise optical filters to reject light at other wavelengths.

The diffractive beam expander may comprise an in-coupling grating 210 and out-coupling gratings 230. The gratings 230 may also be portions of the same grating. The gratings 210, 230 may be implemented on a substantially planar transparent substrate 7. The substrate 7 has a first substantially planar surface and a second substantially planar surface which is substantially parallel to said first planar surface.

The substrate 7 is waveguiding, which means that in-coupled light may propagate within said substrate 7 such that said propagating light may be confined to said substrate 7 by total internal reflections (TIR).

The light source 350 may provide a narrow light beam B4. The narrow beam B4 impinges on the in-coupling grating 210 which diffracts light of said narrow beam into at least two different directions. The in-coupling grating acts as a diffractive beam splitter which provides a first in-coupled beam B5 and a second in-coupled beam B6. The beams B5 and B6 propagating within the substrate 7 are confined to the substrate 7 by total internal reflections.

The first in-coupled beam B5 may substantially correspond to the reflective or transmissive diffraction order −1 and the second in-coupled beam B6 may substantially correspond to the reflective or transmissive diffraction order +1.

The light of the beams B5 and B6 may be coupled out of the substrate 7 by the out-coupling gratings 230. The out-coupling gratings 230 provide the illuminating beams B11, B12.

U.S. Pat. No. 6,580,529 discloses a diffractive beam expander for expanding a light beam in two dimensions.

Figure 5B:
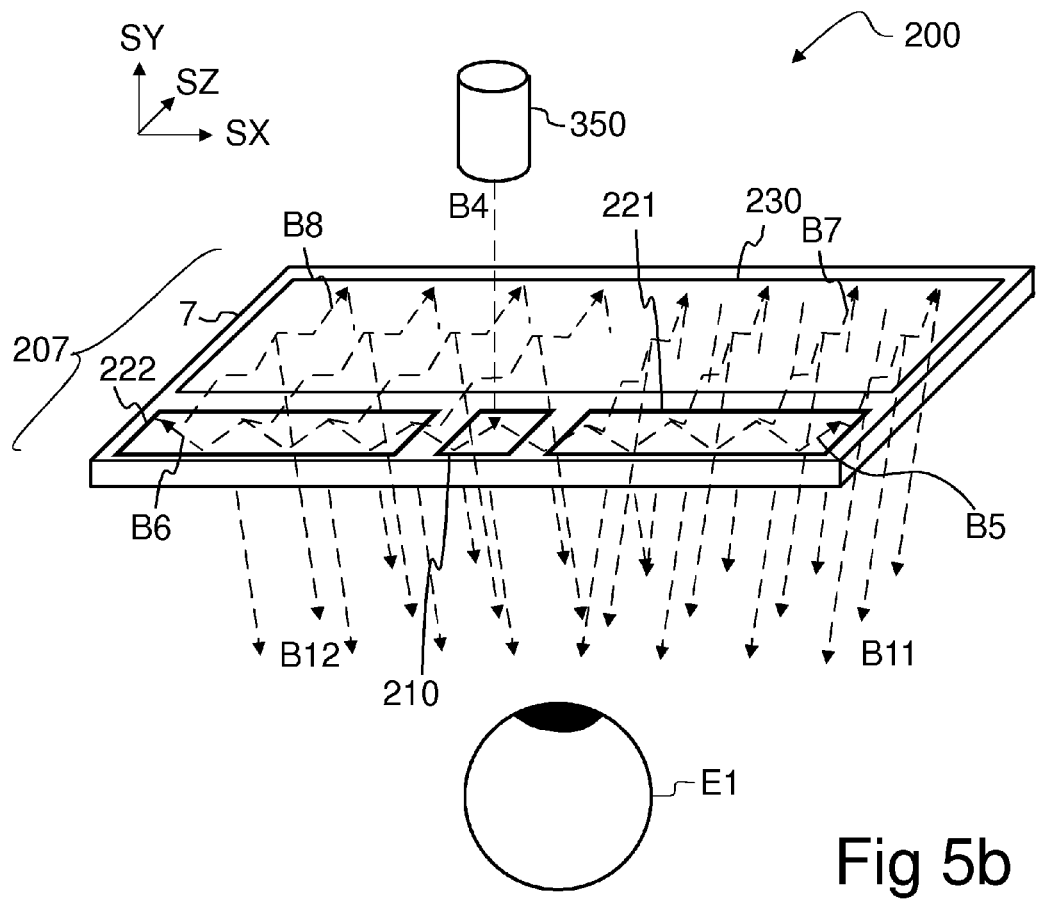
FIG. 5b shows, in a three dimensional view, a diffractive beam expander adapted to provide a first collimated illuminating beam and a second collimated illuminating beam.

Referring to FIG. 5b, the diffractive beam expander 207 may further comprise a first expanding grating 221 and a second expanding grating 222. The first expanding grating 221 may provide a first internal beam B7 by diffracting light of the first in-coupled beam B5. The second expanding grating 221 may provide a second internal beam B8 by diffracting light of the second in-coupled beam B5. The internal beams B7, B8 have been expanded in the direction SX when compared to the original narrow beam B4 provided by the light source 350.

The narrow beam B4 may be substantially perpendicular to the in-coupling grating 210.

The out-coupling grating, out-coupling gratings, or out-coupling grating portions 230 may provide the illuminating beams B11, B12 by diffracting light of the internal beams B7, B8 out of the substrate 7. The illuminating beams B11, B12 may be directed such, and the tracker device 200 may be positioned with respect to the eye E1 such that the illuminating beams B11, B12 impinge on the corneal surface of the eye E1. The out-coupling grating 230 may provide beam expansion in the direction SZ. Consequently, the illuminating beams B11, B12 may now be expanded in the directions SX and SZ when compared to the dimensions of the narrow beam B4.

Figure 6A:
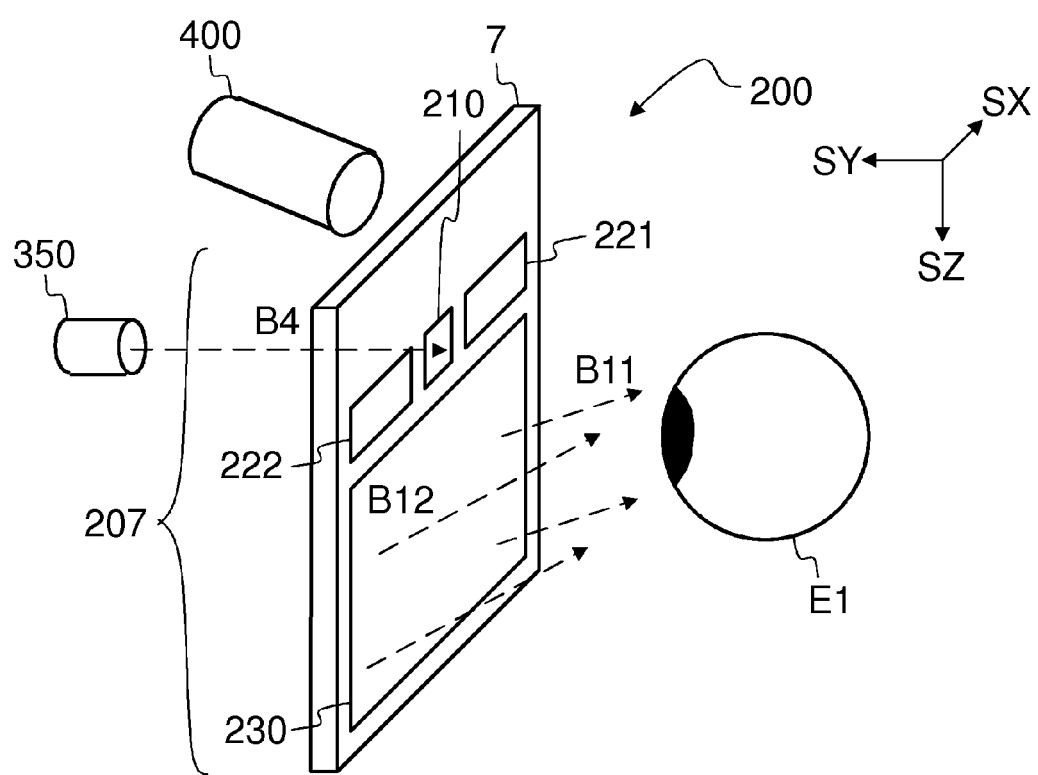
FIG. 6a shows, in a three dimensional view, an eye tracking device comprising a diffractive beam expander.

The gratings 210, 221, 222 and 230 may have substantially linear diffractive features, e.g. a plurality of ridges and/or grooves. The diffractive features of the in-coupling grating 210 may be substantially parallel to the direction SZ. The diffractive features of the out-coupling grating 230 may be substantially parallel to the direction SX. The orientation of diffractive features in the expanding gratings may be selected such that the internal beams B7, B8 have different azimuth angles. Thus, diffraction of the beams B7, B8 at the out-coupling grating 230 provides the illuminating beams B11 and B12 which propagate in different directions, although the orientation of diffractive features at a first grating portion interacting with the beam B7 is the same as the orientation of diffractive features at a second grating portion interacting with the beam B8. Consequently, even the same portion of the grating 230 may be used to diffract light in the direction of the beam B11 and in the direction of the beam B12. Even the same point of the grating 230 may diffract light in the direction of the beam B11 and in the direction of the beam B12. This facilitates providing illuminating beams B11, B12 with overlap almost completely at a predetermined distance from the beam expander 207, i.e. at the preferred distance between the expander and the eye E1. The preferred distance in case of a goggle-type device (see FIG. 19) may be e.g. in the range of 5 to 50 mm FIG. 6a shows a three dimensional view of an eye tracker device 200. The imaging unit 400 may be arranged to monitor the eye E1 through the substrate 7 of the diffractive beam expander 207.

Figure 6B:
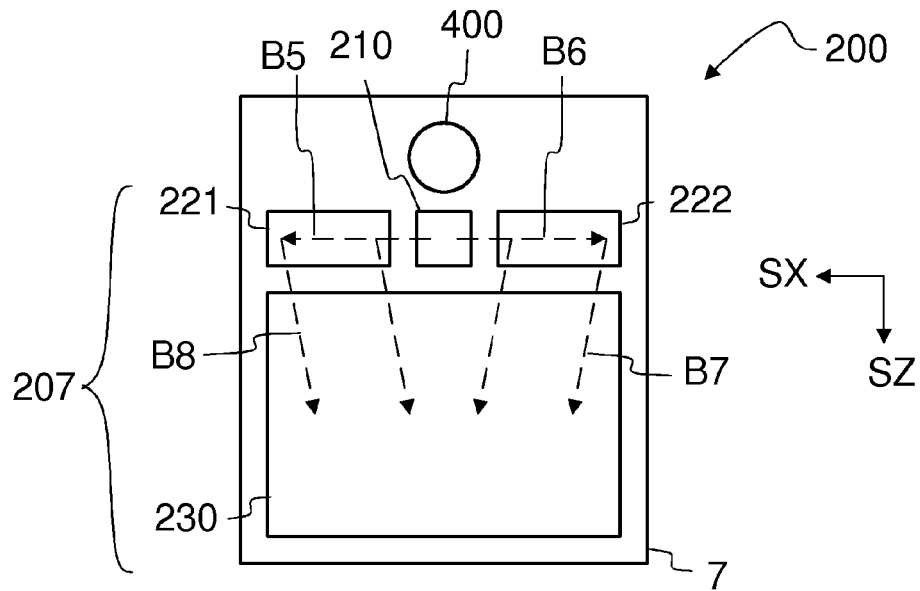
FIG. 6b shows the diffractive beam expander of FIG. 6a, FIG. 6c shows the orientation of diffractive features on the diffractive beam expander of FIG. 6a, FIG. 7a shows a diffractive beam expander.

FIG. 6b shows the positions of the gratings on the diffractive beam expander 207 of the eye tracker device 200 of FIG. 6a.

Figure 6C:
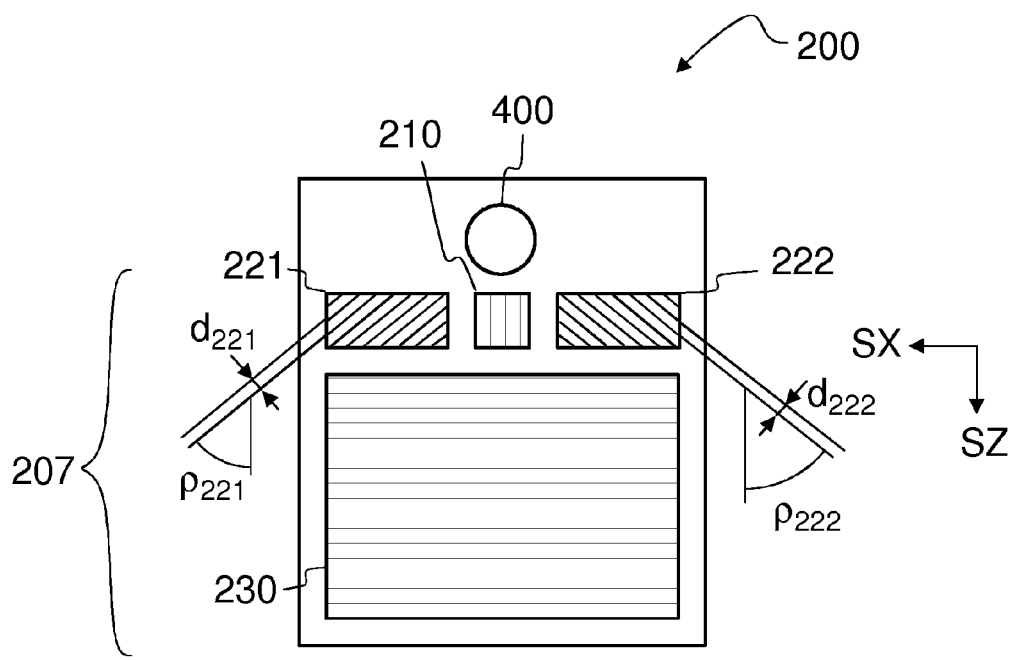

FIG. 6c shows the orientation of diffractive features of the gratings 210, 221, 222, and 230 in the eye tracker device 200 of FIG. 6a. The gratings 210, 221, 222, and 230 may be in a plane defined by the directions SX and SZ. The diffractive features of the in-coupling grating 210 may be substantially parallel to the direction SZ. The diffractive features of the out-coupling grating 230 may be substantially parallel to the direction SZ. The grating periods $d_{221}$ and $d_{222}$ of the expanding gratings 221, 222 and the orientation angles $\rho_{221}$, $\rho_{222}$ of the diffractive features of the expanding gratings 221, 222 may be selected such that the internal beams B7, B8 propagate in different azimuthal directions within the substrate 7.

Figure 7A:
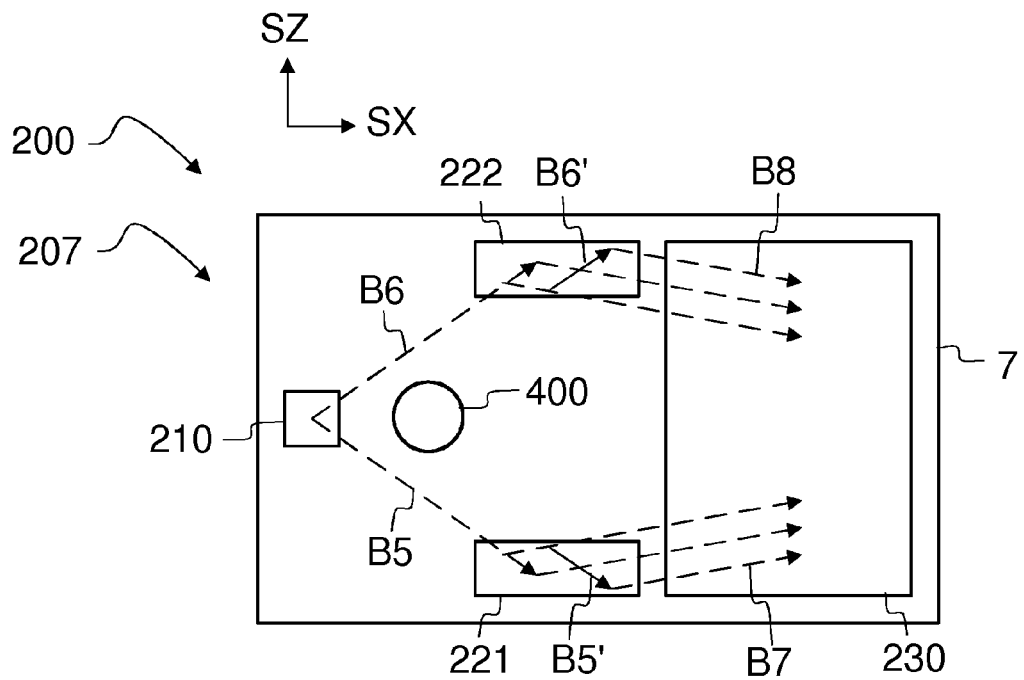
FIG. 7b shows the orientation of diffractive features on the diffractive beam expander of FIG. 7a, FIG. 7c shows, in a three dimensional view, an eye tracking device comprising the diffractive beam expander of FIG. 7a, FIG. 7d shows, in a three dimensional view, an in-coupling grating arranged to diffract light at least in three different directions.

FIG. 7a shows another layout of the gratings 210, 221, 222, 230. Light B8 diffracted from the expanding grating 221 may impinge on the same grating 221 again, thereby providing an auxiliary beam B5' which propagates in the same direction as the original in-coupled beam B5. Light of the auxiliary beam B5' may provide further light rays which propagate in the direction of the internal beam B7. The expanding grating 222 may provide one or more auxiliary beams B6' in a similar fashion. Thus, the expanding gratings 221, 222 provide internal beams B7, B8 which have been expanded in the direction SZ.

Figure 7B:
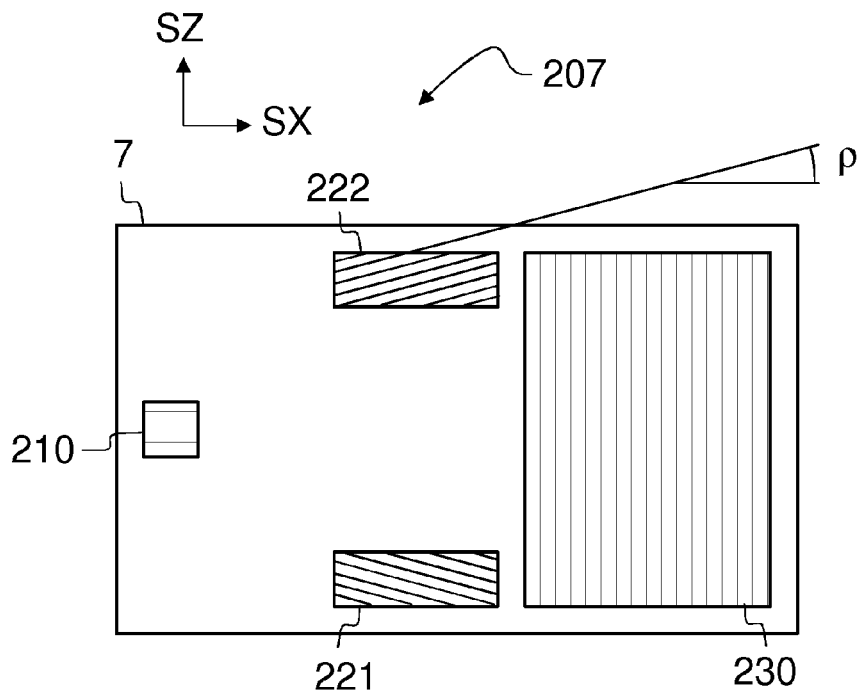

The narrow beam B4 emitted from the light source 350 may be inclined with respect to the in-coupling grating 210 so that the in-coupled beams B5, B6 do not propagate in opposite directions within the substrate 7. The azimuth angle of the beam B5 may be e.g. in the range of −90 to −45 degrees and The azimuth angle of the beam B6 may be e.g. in the range of 45 to 90 degrees The hatch patterns in FIG. 7b show schematically the orientation of the diffractive features in the gratings 210, 221, 222, 230. The orientation of the diffractive features in the gratings 221 and 222 may be selected e.g. according to eq. (1):

$$\frac{\lambda}{2d_{221}} = \left| -\frac{\lambda}{d_{210}} \cos\rho + \sin\theta_{B4} \sin\rho \right|,$$

where $\theta_{B4}$ is the zenith angle of the beam B4 outside the substrate 7, $\rho$ is the angle between the orientation of the diffractive features of the grating 210 and the diffractive features of the grating 221, $\lambda$ denotes the wavelength, $d_{221}$ denotes the grating period of the grating 221, and $d_{210}$ denotes the grating period of the grating 210. The angle $\rho$ of the grating lines of 222 and 221 may be e.g. in the range of 10-30 degrees.

Figure 7C:
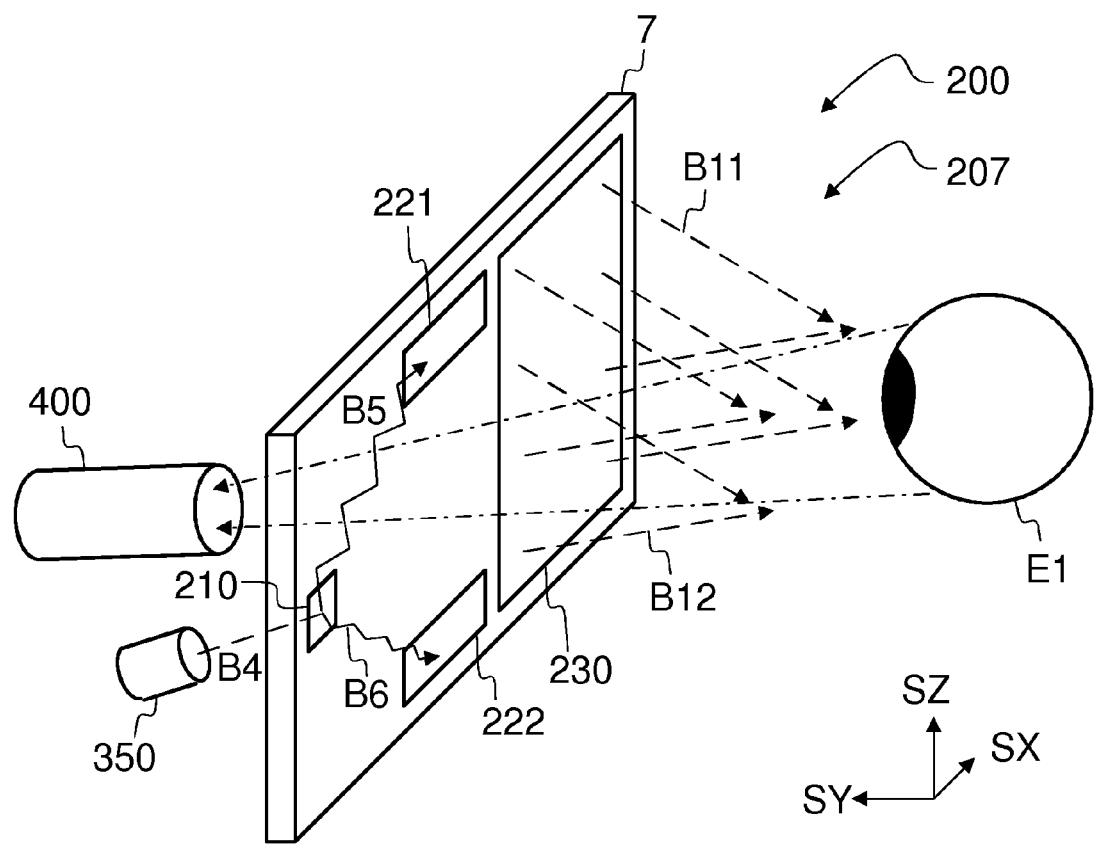

FIG. 7c shows in a three dimensional view the eye tracker device 200 of FIGS. 7a and 7b.

Figure 7D:
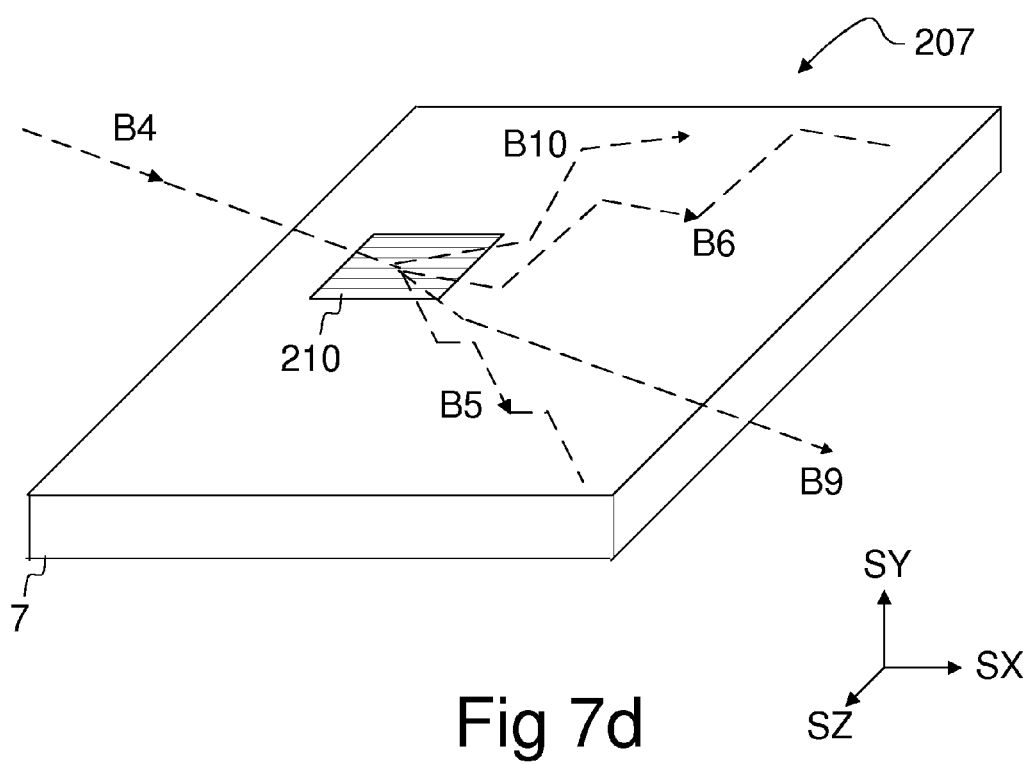

Referring to FIG. 7d, the in-coupling grating may diffract light of the beam B4 into three or more different directions. For example, the in-coupled beams B5 and B6 may be formed by diffractions in the diffraction orders −1 and +1, and a third beam B9 may be formed by diffraction in the zeroth diffraction order. The in-coupled beams B5 and B6 propagate within the substrate 7 towards the out-coupling grating 230 and/or towards expanding grating portions 221, 222, in order to form illuminating beams B11, B12 coupled out of the substrate 7.

The third beam B9 corresponding to the zeroth diffraction order impinges on the opposite plane of the substrate at such an angle that it is not confined to the substrate 7 by total internal reflection. Thus, the beam B9 is transmitted through the substrate 7 and it is coupled out of the substrate 7.

The in-coupling grating may diffract light of the beam B4 e.g. also in the diffraction order 2 in order to provide a further in-coupled beam B10 which may propagate within the substrate 7 towards the out-coupling grating 230 and/or towards a further expanding grating portions (not shown) in order to form a third illuminating beam (not shown), which is coupled out of the substrate 7 towards the eye. A further in-coupled beam may be provided also by diffraction in the diffraction order −2.

The gaze direction may be determined using three or more different illuminating beams propagating in different directions. In case of three illuminating beams, the gaze direction detecting algorithm developed for two beams may be used three times. The first time by using the a first illuminating beam and a second illuminating beam, the second time by using the first illuminating beam and a third illuminating beam, and the third time by using the second illuminating beam and the third illuminating beam. The zenith angles of the three determined gaze directions may be e.g. averaged in order to improve accuracy. The azimuth angles of the three determined gaze directions may be e.g. averaged in order to improve accuracy.

Figure 8A:
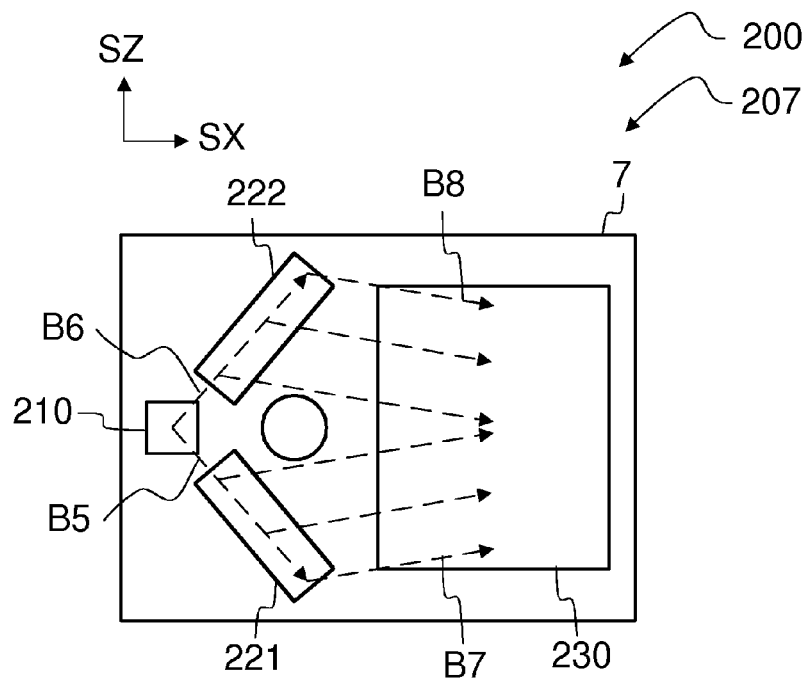
FIG. 8a shows a diffractive beam expander.

FIG. 8a shows yet another layout of a diffractive beam expander 207 wherein the perimeter of the expanding gratings 221, 222 is inclined with respect to the direction of the diffractive features of the out-coupling grating 230. The narrow beam B4 emitted from the light source 350 may be inclined with respect to the in-coupling grating 210 to provide in-coupled beams B5, B6 which are inclined with respect to the direction of the diffractive features of the out-coupling grating 230. The elongated expanding gratings 221, 222 may be substantially aligned with the directions of the in-coupled beams B5, B6.

Figure 8B:
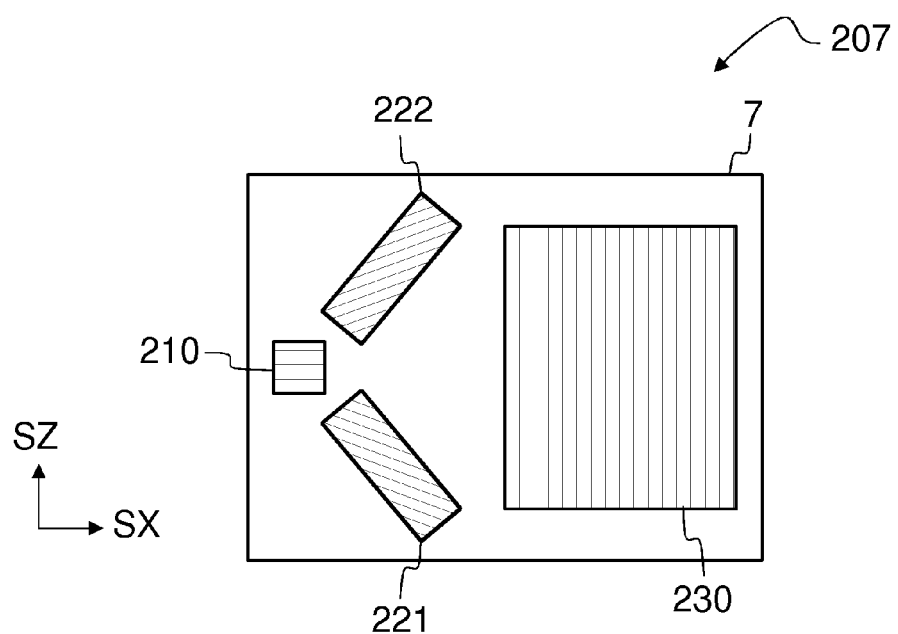
FIG. 8b shows the orientation of diffractive features on the diffractive beam expander of FIG. 8a, FIG. 9 shows, in a three dimensional view, a virtual display device comprising a diffractive beam expander.

The hatch patterns in FIG. 8b show the approximate orientation of the diffractive features in the gratings 210, 221, 222, 230 in the device of FIG. 8a.

Figure 9:
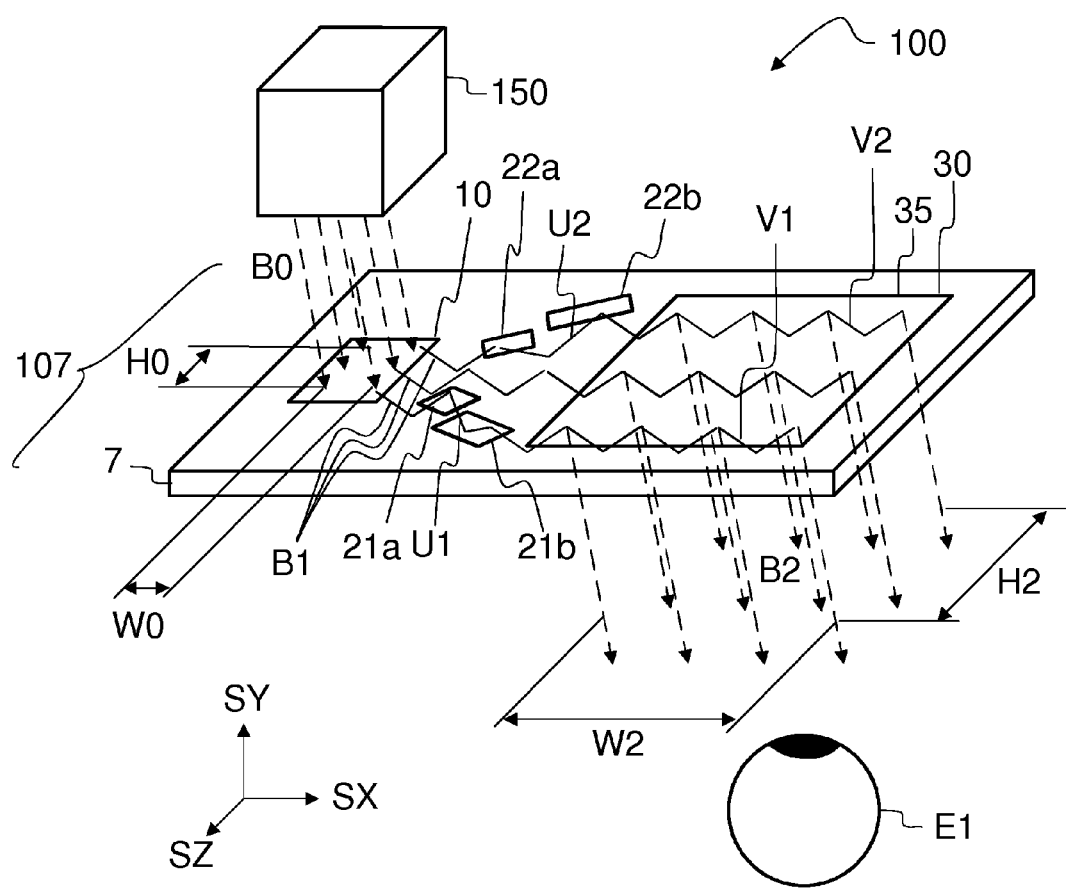
Figure 10A:
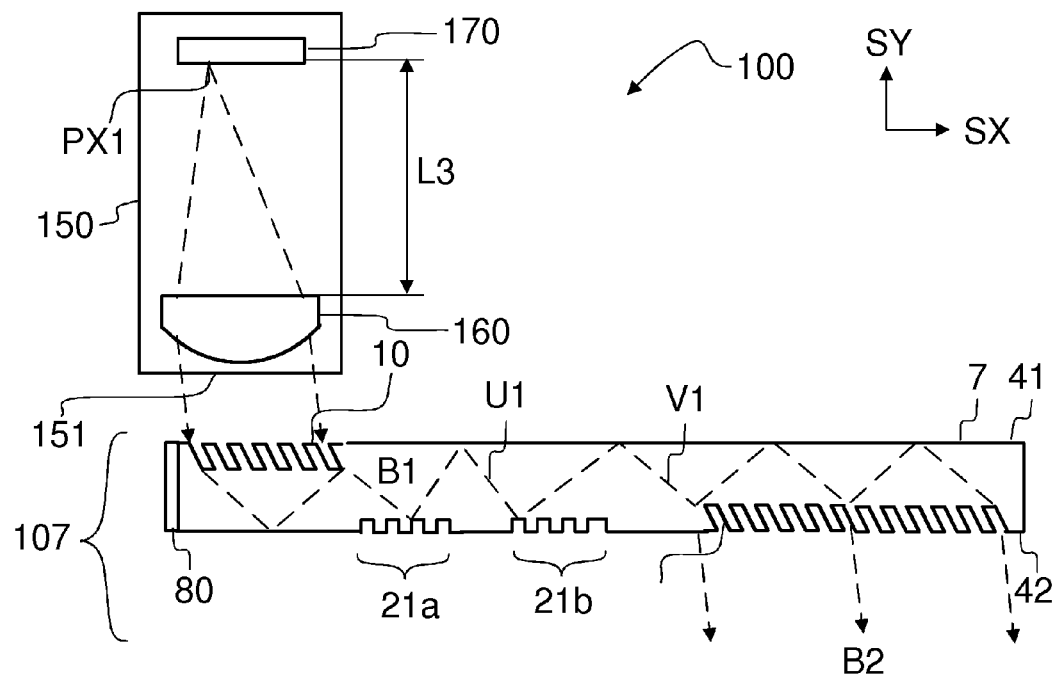
FIG. 10a shows, in a side view, the virtual display device of FIG. 9.

FIG. 9 shows a virtual display device 100. The virtual display device 200 may comprise an optical engine 150 and a diffractive beam expander 107. The optical engine 150 may comprise a micro-display 170 and imaging optics 160 (FIG. 10a). The imaging optics 160 converts a real image 605 (FIG. 10b) formed by the micro-display 170 into a virtual image 1002 (FIG. 19) which is observable through a viewing aperture 35 of the diffractive beam expander 107.

The diffractive beam expander 107 may comprise an input grating 10, at least one beam-deflecting portion 21a, 22a, at least one direction-restoring portion 21b, 22b, and an output grating 30. The gratings 10, and the portions 21a, 21b, 22a, 22b may be implemented on a substantially planar waveguiding substrate 7.

The optical engine provides an input beam B0. The input beam B0 impinging on the input grating 10 may be coupled into the substrate 7 such that a corresponding in-coupled beam B1 propagates within said substrate towards the beam-deflecting portions 21a, 22a.

The planar surfaces of the waveguiding substrate 7 are in planes defined by the directions SX and SZ.

A part of the in-coupled beam B1 impinges on a first beam-deflecting grating portion 21a, which diffracts light towards a first direction-restoring grating portion 21b providing a first deflected light beam U1. The restoring portions 21b diffracts light of the beam U1 providing a first restored light beam V1. The restored beam V1 has been shifted with respect to the original in-coupled beam B1 and it propagates substantially in the same direction as the original in-coupled beam B1.

A part of the in-coupled beam B1 may impinge on a second beam-deflecting grating portion 22a, which may diffract light towards the second direction-restoring grating portion 22b providing a second deflected light beam U2. The restoring portion 22b diffracts light of the beam U2 providing a second restored light beam V2. Also the second restored beam V2 has been shifted with respect to the original in-coupled beam B1 and it propagates substantially in the same direction as the original in-coupled beam B1.

A part of the original in-coupled beam B1 may propagate within the substrate 7 without being diffracted by the portions 21a, 21b, 22a, 22b.

The undiffracted part of the beam B1, the restored beam V1 and/or the restored beam V2 may together from an enlarged beam which propagates in the same direction as the original in-coupled beam B1.

The enlarged beam may be subsequently coupled out of the substrate 7 by the output grating 30 to provide an output beam B2 which is expanded in two directions SX and SZ when compared to the dimensions of the input beam B0. The output beam B2 may be arranged to impinge on the eye E1 of an observer.

The height H2 of the output beam B2 is greater than the height H0 of the input beam B0. Thus, the diffractive beam expander 107 provides beam expansion in the direction SZ. The width W2 of the output beam B2 may be greater than the width W0 of the input beam B0. The maximum height H2 and the maximum width W2 of the output beam B2 are limited by the dimensions of the viewing aperture 35. The height and the width of the input grating 10 may be selected to be substantially equal to or greater than the dimensions of the input beam B0, in order to maximize the efficiency of coupling light into the substrate 7.

The gratings and the grating portions are diffractive elements. The gratings and the grating portions may be e.g. surface relief gratings implemented by molding or embossing on either of the planar surfaces 41, 42 (FIG. 10a). The profile of the gratings may be e.g. sinusoidal, binary rectangular or blazed. Yet, the profile of the gratings may be binary slanted or sinusoidal slanted. One or more gratings and/or portions may be embedded within the substrate 7. The gratings 10, 30 and the grating portions 21a, 21b, 22a, 22b may be in one or more planes defined by the directions SX and SY.

The substrate 7 may comprise or consist of e.g. polycarbonate, polymethyl methacrylate (PMMA), or glass.

Referring to FIG. 10a, the optical engine 150 may comprise a micro-display 170 and imaging optics 160. The imaging optics 160 may comprise one or more optical elements such as lenses, mirrors, prisms or diffractive elements. Light rays transmitted from a point PX1 of the micro-display 170 are substantially collimated by the imaging optics 160 to form parallel rays of light which constitute the beam B0 provided by the optical engine 150. The distance L3 between the micro-display 170 and the imaging optics 160 is set such that the pixels of the micro-display 170 are substantially at the focal distance of the imaging optics 160. A plurality of beams B0 are provided in order to display a virtual image, which consists of a plurality of pixels.

At least one beam B0 transmitted from the output aperture 151 of the optical engine 150 impinges on the input grating 10 of the diffractive beam expander 107. Light of the input beam B0 is coupled into the waveguiding substrate 7 by the input grating 10. The in-coupled light propagates within the substrate 7 as the in-coupled beam B1. A part of the in-coupled beam B1 interacts with the first deflecting grating portion 21a providing the deflected beam U1. A part of the deflected beam U1 interacts with the restoring grating portion 21b providing the first restored beam V1. A part of the in-coupled beam B1 may remain undiffracted (not shown in FIG. 10a). The output grating 30 diffracts the expanded output beam B2 towards the eye E1 of the observer.

Figure 19:
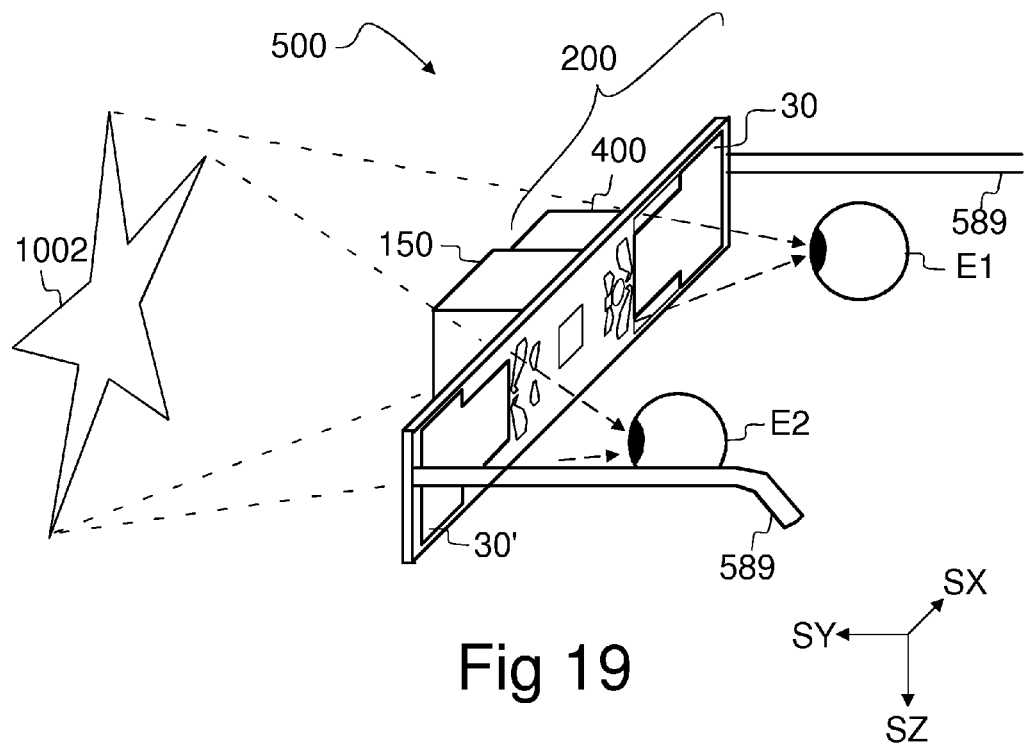
FIG. 19 shows a bi-ocular virtual display device.

The enlarged light beams B2 provided by the diffractive beam expander 107 provide for a viewer an impression of a virtual image 1002 displayed at an infinite distance from the viewer. However, as a phenomenon, human viewers typically perceive that the displayed virtual image 1002 is only a few meters away from them, despite the infinite distance. The virtual image 1002 may be e.g. a star pattern as shown in FIG. 19.

The diffractive beam expander 107 may be mono-ocular, i.e. it may have only one output grating 30. The input grating 10, the output grating 30 and/or the grating portions 21a, 21b, 22a, 22b may be slanted or blazed surface relief gratings in order to maximize the efficiency of coupling light into the substrate 7 and out of the substrate 7. The diffractive beam expander 107 may comprise one or more optically absorbing structures 80 to eliminate stray light.

The substrate 7 has a first substantially planar surface 41 and a second substantially planar surface 42, which is substantially parallel to said first planar surface 41. The gratings 10, 30 and the portions 21a, 21b, 22a, 22b may be on the same planar surface 41, 42, or on opposite surfaces 41, 42. The input beam B0 may also be transmitted through the substrate 7 before impinging on the input grating 10.

The micro-display 170 may be e.g. a liquid crystal display, an array of micromechanically movable mirrors, an array of light emitting diodes, or a unit comprising at least one movable and modulatable light-emitting point.

Figure 10B:
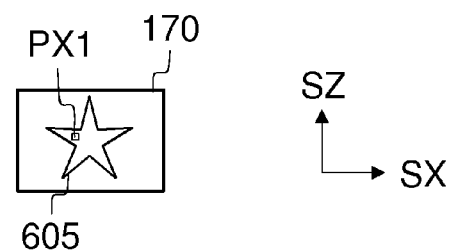
FIG. 10b shows an image generated by a micro display.

FIG. 10b shows a real image 605 formed on the micro-display 170. The real image may be formed of light-emitting pixels or light-emitting points PX1.

The optical engine 150 may also comprise a light-emitting point to provide a light beam and a beam-steering unit to rapidly vary the direction of said beam, wherein optical power provided by said light emitting point may be modulated based on the direction of said beam. The beam-steering unit may comprise e.g. one or more turning reflectors to change the direction of the beam. In other words, the optical engine 150 may also directly provide a virtual image by using a scanning method.

Figure 11A:
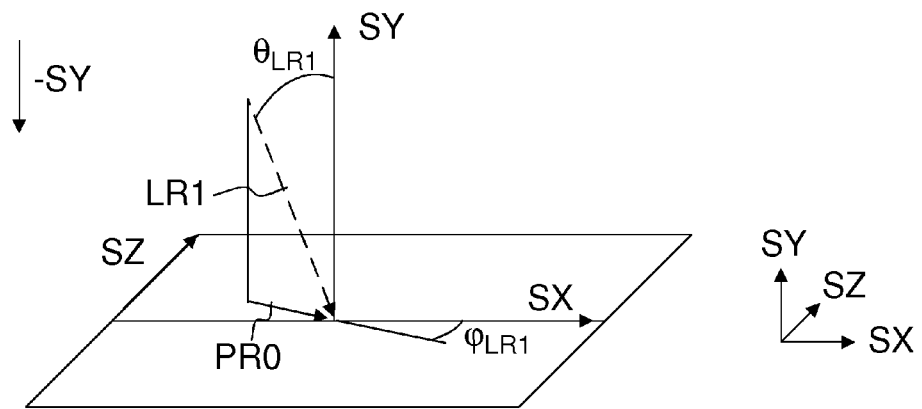
FIG. 11a shows, in a three dimensional view, zenith and azimuth angles of a light ray or of a light beam.

FIG. 11a shows the azimuth angle $\phi_{LR1}$ of a light ray LR1 and the zenith angle $\theta_{LR1}$ in the coordinate system defined by the directions SX–SY–SZ. In general, the zenith angle is an angle between the direction of a light ray or beam and the direction –SY. The direction –SY is opposite the direction SY.

The azimuth angle is an angle between the projection PR0 and the direction SX, wherein said projection PR0 is the projection of the direction of the light ray LR1 in a plane defined by the directions SX and SZ. The projection PR0 forms the left side of the azimuth angle.

Figure 11B:
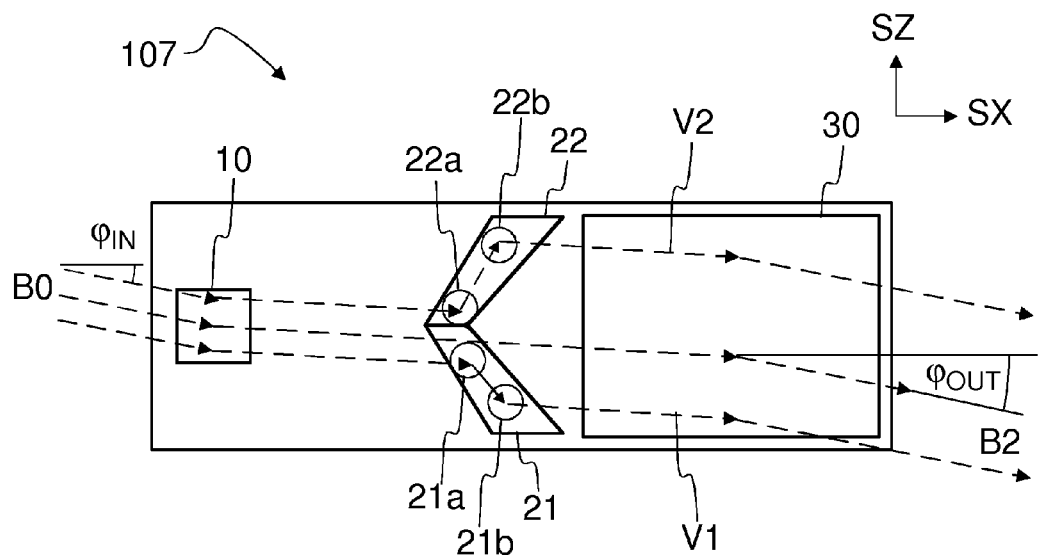
FIG. 11b shows, in a top view, the azimuth angle of an in-coupled beam and the azimuth angle of an out-coupled beam.

Referring to FIG. 11b, the projection of the input beam B0 on the SX-SZ-plane has an azimuth angle $\phi_{IN}$ with respect to the direction SX. The projections of the in-coupled beam B1 and the restored beams V1, V2 have an azimuth angle with respect to the direction SX. The projection of the output beam B2 has an azimuth angle $\phi_{OUT}$ with respect to the direction SX.

An intermediate grating 21 may comprise the deflecting portion 21a and a restoring portion 21b. A second intermediate grating 22 may comprise the deflecting portion 22a and a restoring portion 22b.

Figure 11C:
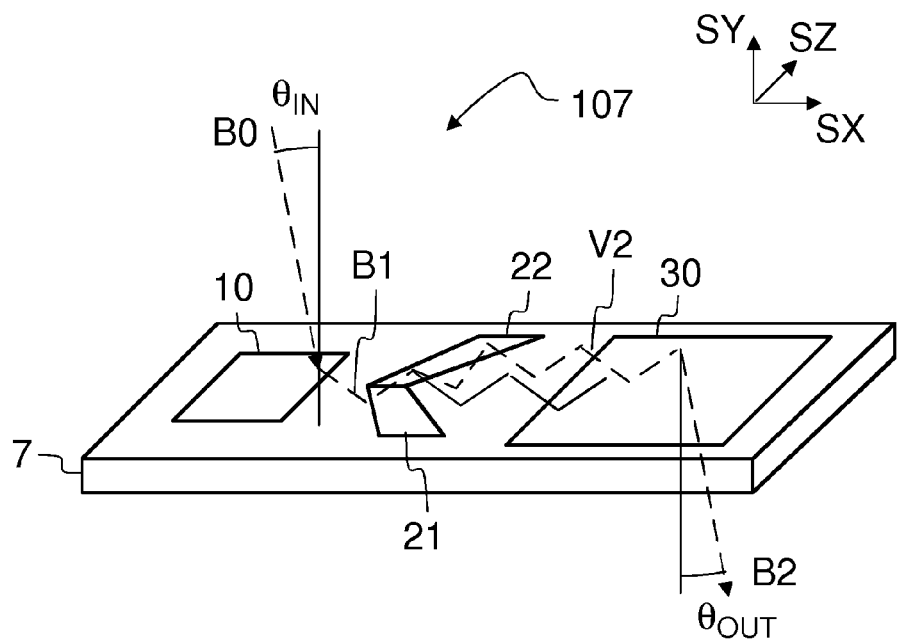
FIG. 11c shows, in a in a three dimensional view, the zenith angle of an in-coupled beam and the zenith angle of an out-coupled beam.

Referring to FIG. 11c, the direction of the input beam B0 has a zenith angle $\theta_{IN}$ with respect to the direction −SY. The direction of the output beam B2 has a zenith angle $\theta_{OUT}$ with respect to the direction −SY.

The orientation of the diffractive features of the gratings 10, 30 and the grating portions 21a, 21b, 22a, 22b and the grating periods of the gratings 10, 30 and the grating portions 21a, 21b, 22a, 22b may be selected such that the zenith angle $\theta_{IN}$ of the input beam B0 is substantially equal to the zenith angle $\theta_{OUT}$ of the output beam B2, and such that the azimuth angle $\phi_{IN}$ of the input beam B0 is substantially equal to the azimuth angle $\phi_{OUT}$ of the output beam B2.

In principle, the output beam B2 may also be coupled out of the substrate 7 upwards in the direction SY. The orientation of the diffractive features of the gratings 10, 30 and the grating portions 21a, 21b, 22a, 22b and the grating periods of the gratings 10, 30 and the grating portions 21a, 21b, 22a, 22b may be selected such that the direction of the input beam B0 is substantially parallel to the direction of the output beam B2.

Now, because the direction of the light beams corresponding to the displayed virtual image 1002 is preserved, the beam expander 107 may expand the exit pupil of the optical engine 150. The plurality of light beams B2 impinging on the eye E1 of the viewer create an impression of the same virtual image as when viewing the virtual image provided by the optical engine 150 without the beam expander 107. However, thanks to the beam expander 107, the viewer has a considerable freedom to move his eye E1 with respect to the virtual display unit 200 in the directions SX, SZ, and SY.

Next, a few alternatives for implementing a diffractive beam expander 107 suitable for expanding an exit pupil of a virtual display will be discussed.

Figure 12A:
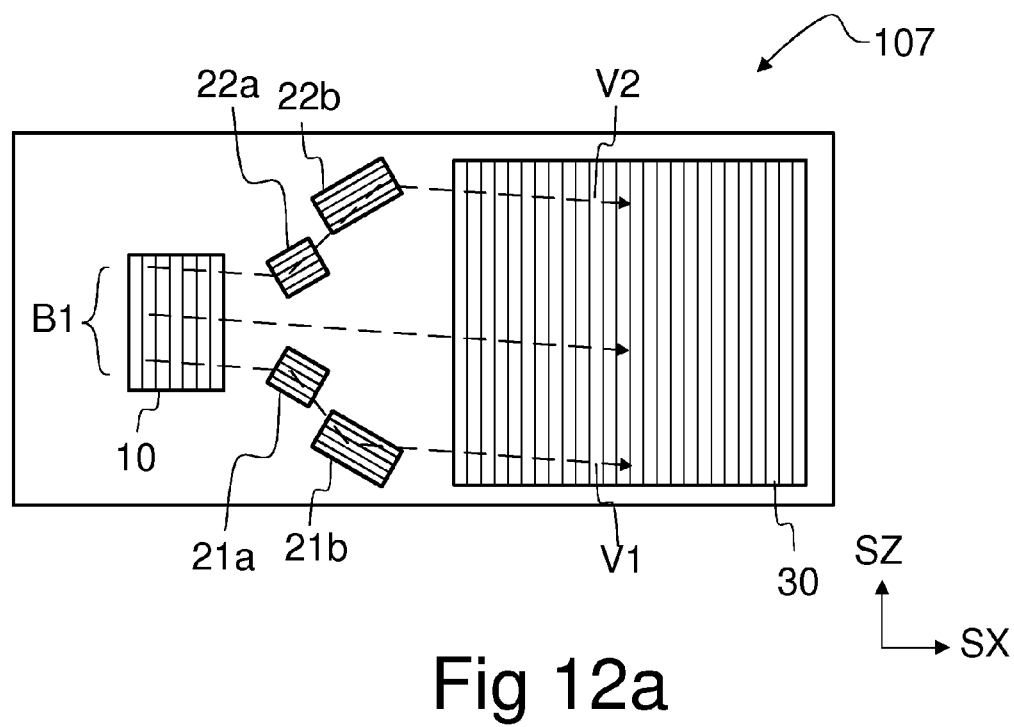
FIG. 12a shows, in a top view, a diffractive beam expander comprising deflecting and restoring intermediate grating portions.
Figure 12B:
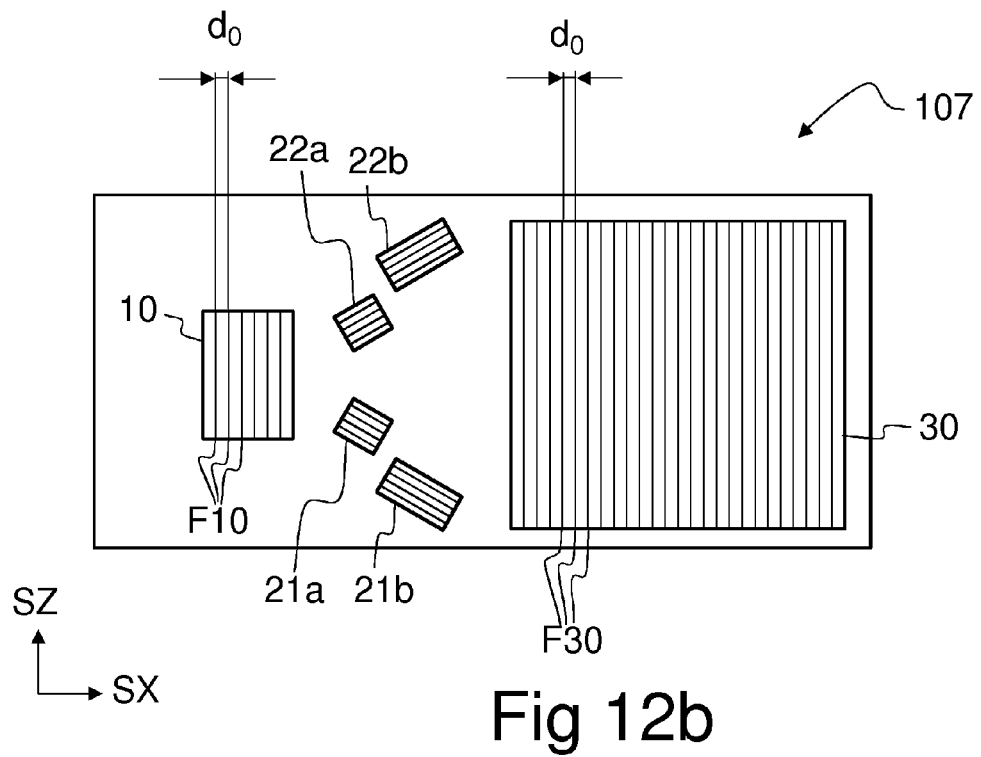
FIG. 12b shows, in a top view, the orientation of diffractive features on the diffractive beam expander of FIG. 12a, FIG. 12c shows, in a top view, the orientation of diffractive features on the diffractive beam expander of FIG. 12a, FIG. 13 shows, in a top view, a diffractive beam expander comprising deflecting and restoring intermediate grating portions.
Figure 12C:
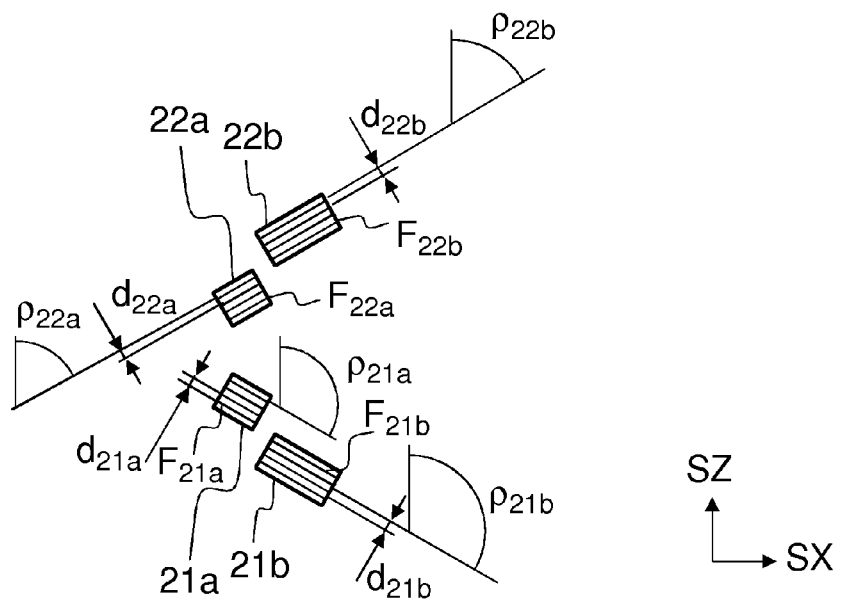

Referring to FIG. 12a, the diffractive beam expander 107 may comprise an input grating 10, the deflecting portions 21a, 22a, restoring portions 21b, 22b, and an output grating 30. The hatch patterns in FIG. 12b show the approximate orientation of the diffractive features of the gratings 10, 30 and the grating portions 21a, 21b, 22a, 22b. The gratings 10, 30 and the grating portions 21a, 21b, 22a, 22b may comprise substantially linear diffractive features, e.g. a plurality of microscopic grooves and/or ridges. The features F10 of the grating 10 and the features F30 of the grating 30 may be substantially parallel to the direction SZ. The grating period of the input grating 10 and the output grating 30 is $d_0$. Referring to FIG. 12c, the portions 21a, 21b, 22a, 22b have substantially linear diffractive features $F_{21a}$, $F_{21b}$, $F_{22a}$, $F_{22b}$, which have grating periods $d_{21a}$, $d_{21b}$, $d_{22a}$, $d_{22b}$, and orientation angles $\rho_{21a}$, $\rho_{21b}$, $\rho_{22a}$, $\rho_{22b}$, respectively. An orientation angle defines herein the direction of the diffractive features with respect to the direction of the diffractive features of the grating 10.

The first deflecting grating portion 21a has a plurality of diffractive features $F_{21a}$, which have an angle $\rho_{21a}$ with respect to the direction SZ. The first deflecting grating portion 21a has a grating period $d_{21a}$.

The second deflecting grating portion 22a has a plurality of diffractive features $F_{22a}$, which have an angle $\rho_{22a}$ with respect to the direction SZ. The second deflecting grating portion 22a has a grating period $d_{21b}$.

The first restoring grating portion 21b has a plurality of diffractive features $F_{21b}$, which have an angle $\rho_{21b}$ with respect to the direction SZ. The first restoring grating portion 21b has a grating period $d_{21b}$.

The second restoring grating portion 22b has a plurality of diffractive features $F_{22b}$, which have an angle $\rho_{22b}$ with respect to the direction SZ. The second restoring grating portion 22b has a grating period $d_{22b}$.

The relationship between the orientation angle $\rho$ of the diffractive features and the grating period of said features is given by $$d = \frac{d_0}{A_0 \cos \rho},$$

where $d_0$ is the grating period of the grating 10, and $A_0$ is a constant having a value in the range of 1.8 to 2.2. In particular, the constant $A_0$ may be substantially equal to two. The grating periods of the grating portions 21a, 21b, 22a, 22b, 21c, 22c may now be solved using eq. (2).

The grating periods of the grating portions 21a, 21b, 22a, 22b, 21c, 22c may be selected using eq. (2) such that diffraction is allowed only in the zeroth and in the first diffraction modes. The sign of the first order diffraction depends on the chosen coordinates.

The angle $\rho_{21a}$ between the direction of the diffractive features $F_{21a}$ of said first deflecting grating portion 21a and the direction SZ of the diffractive features $F_{10}$ of said input grating 10 may be in the range of 55 to 65 degrees. In particular, the orientation angle $\rho_{21a}$ may be substantially equal to 60 degrees. The orientation angle $\rho_{22a}$ may be substantially equal to 120 degrees, respectively.

The first deflecting portion 21a and the first restoring portion 21b may have the same orientation of diffractive features and the same grating period. The second deflecting portion 22a and the second restoring portion 22b may have the same orientation of diffractive features and the same grating period. The first auxiliary reflecting portion 21c (See FIG. 15a) and the first restoring portion 21b may have the same orientation of diffractive features and the same grating period. The second auxiliary reflecting portion 22c (see FIG. 15a) and the second restoring portion 22b may have the same orientation of diffractive features and the same grating period.

Figure 13:
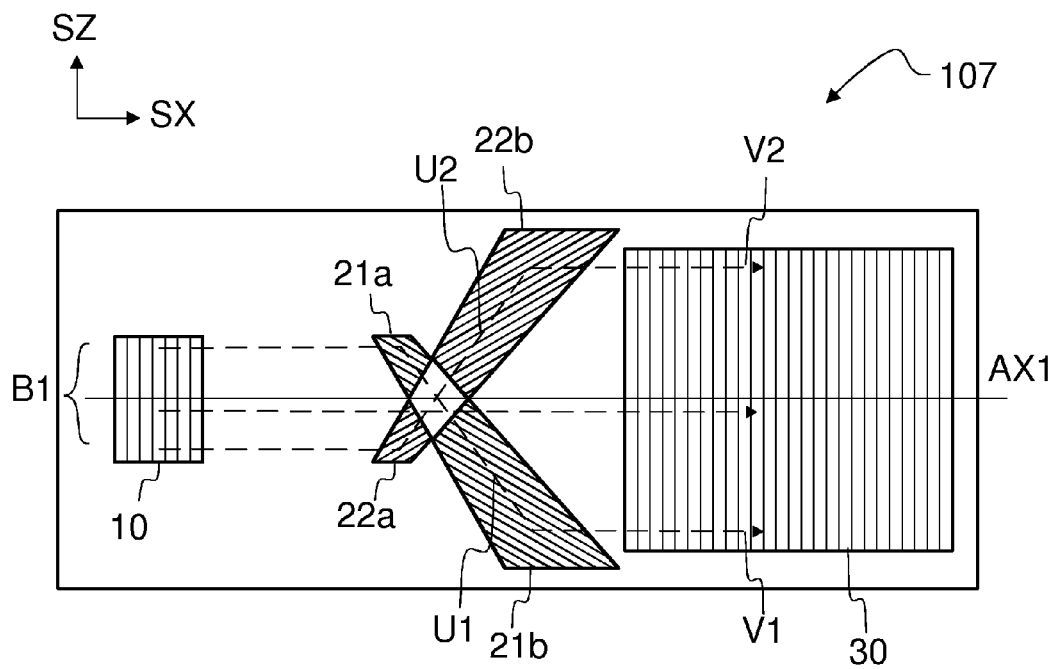

Referring to FIG. 13, a line AX1 may intersect the input grating 10 and the output grating 30. In particular, the line AX may pass through the center of the input grating 10 and through the center of the output grating 30. The deflection portion 21a and the restoring portion 21b may be on different sides of the line AX1. Also the deflecting portion 22a and the restoring portion 22b may be on different sides of the line AX1. Consequently, the deflected beams U1 and U2 cross the line AX1.

Figure 14:
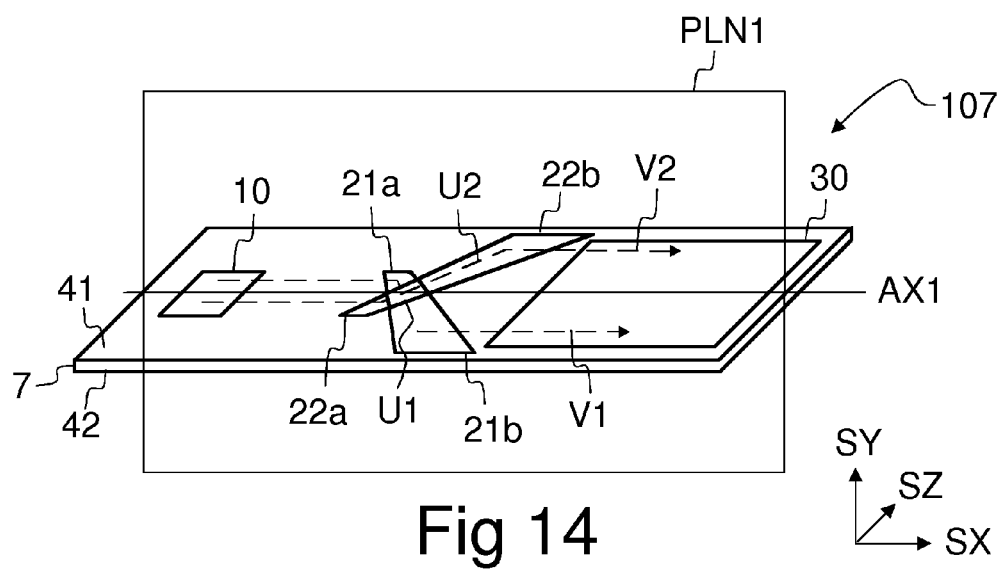
FIG. 14 shows, in a in a three dimensional view, propagation of light beams in the diffractive beam expander of FIG. 13.

Referring to FIG. 14, the line AX1 is, in fact, a projection of a plane PLN1. The deflection portion 21a and the restoring portion 21b may be on different sides of the plane PLN1 defined by the directions SX and SY. Also the deflecting portion 22a and the restoring portion 22b may be on different sides of the plane PLN1. Consequently, the deflected beams U1 and U2 pass through the plane PLN1.

Thus, the diffractive beam expander 107 may comprise:
a substantially planar waveguiding substrate 7,
an input grating 10 to provide an in-coupled beam B1 propagating within said substrate 7 by diffracting light of an input beam B0 into said substrate 7,
a first deflecting grating portion 21a to provide a first deflected beam U1 by diffracting a part of said in-coupled beam B1 such that the difference between the azimuth angle of said first deflected beam U1 and the azimuth angle of said in-coupled beam B1 is negative, said first deflecting grating portion 21a comprising substantially linear diffractive features,
a second deflecting grating portion 22a to provide a second deflected beam U2 by diffracting a part of said in-coupled beam B1 such that the difference between the azimuth angle of said second deflected beam U2 and the azimuth angle of said in-coupled beam B1 is positive, said second deflecting grating portion 22a comprising substantially linear diffractive features, the diffractive features of said second deflecting grating portion having a different orientation than the diffractive features of said first deflecting grating portion 21a,
a first restoring grating portion 21b to provide a first restored beam V1 by diffracting light of said first deflected beam U1,
a second restoring grating portion 22b to provide a second restored beam V2, said second restored beam V2 being substantially parallel to said first restored beam V1, and
an output grating 30 to provide an out-coupled beam B2 by diffracting light of said first restored beam V1 and said second restored beam V2 out of said substrate 7, said output beam B2 being substantially parallel to said input beam B0.

Said first deflecting grating portion 21a and said second restoring grating portion 22b may be on a first side of the reference plane PLN1, and said second deflecting grating portion 22a and said first restoring grating portion 21b may be on a second side of said reference plane PLN1, said reference plane PLN1 being substantially perpendicular to the plane of said input grating 10.

Figure 15A:
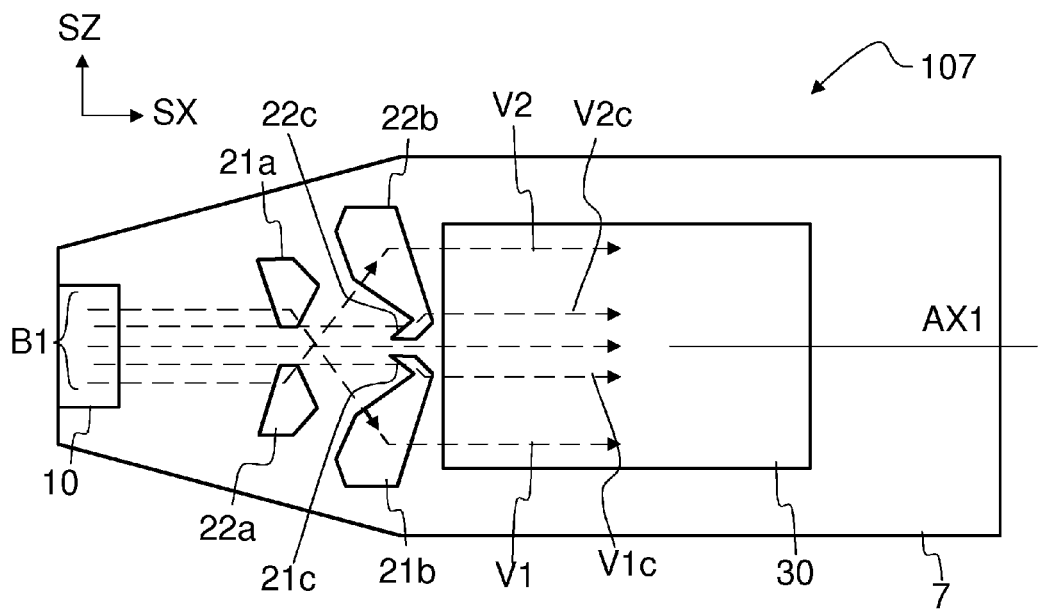
FIG. 15a shows, in a top view, a diffractive beam expander for displaying virtual images.

Referring to FIG. 15a, the diffractive beam expander 107 may comprise an input grating 10, an output grating 30, deflecting portions 21a, 22a, and restoring portions 21b, 22b. In addition, the beam expander 107 may have auxiliary deflecting portions 21c, 22c. The first auxiliary deflecting portion diffracts light of the in-coupled beam B1 towards the first restoring portion 21b. The second auxiliary deflecting portion diffracts light of the in-coupled beam B1 towards the second restoring portion 22b. The restoring portions 21b, 22b diffract the light again, providing auxiliary restored beams V1c and V2c, which are substantially parallel to the original in-coupled beam B1 and the restored beams V1 and V2.

The portions 21a, 22b and 22c may be on a first side of a plane PLN1, and the portions 22a, 21b, and 21c may be on a second side of said plane PLN, said plane PLN1 being substantially perpendicular to the plane of the input grating 10. The line AX1 is the projection of said plane PLN1 (see FIG. 14).

Figure 15B:
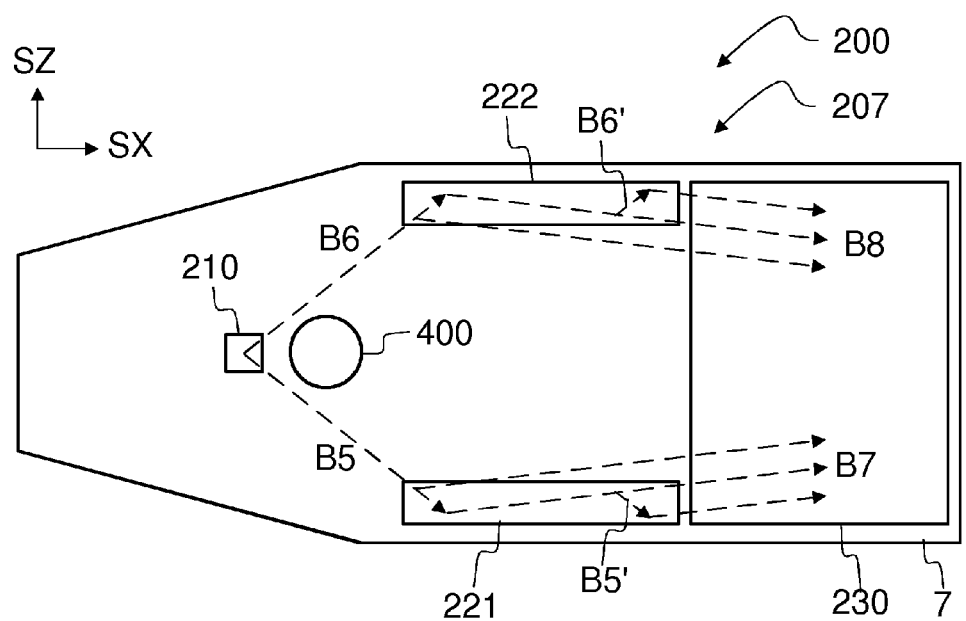
FIG. 15b shows, in a top view, a diffractive beam expander for providing two collimated light illuminating beams.

Referring to FIG. 15b, the substrate 7 of FIG. 15a may also comprise an in-coupling grating 210, expanding gratings 221, 222, and an out-coupling grating 230 for providing the illuminating light beams B11, B12 needed for eye tracking. The gratings 210, 221, 222 and 230 form a second diffractive beam expander 207 which splits a narrow collimated beam impinging on the in-coupling grating 210 into at least two parts and provides the two enlarged beams B11, B12, which propagate in different directions (see also FIGS. 5b and 7c).

Figure 15C:
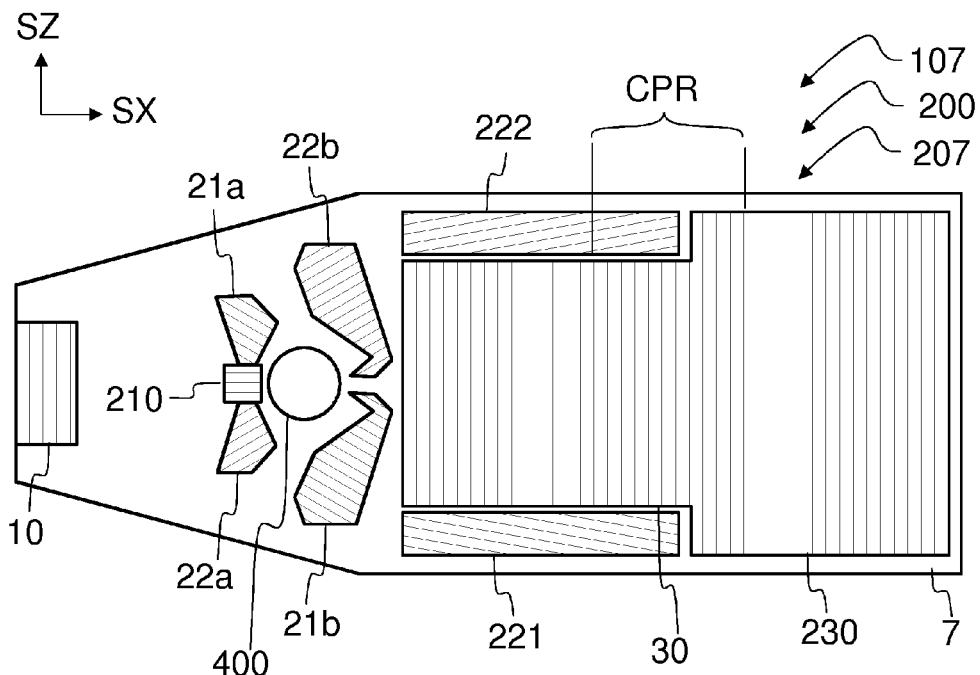
FIG. 15c shows, in a top view, a substrate comprising a first diffractive beam expander for providing two collimated illuminating light beams and a second diffractive beam expander for displaying virtual images.

The hatching in FIG. 15c shows, by ways of example, the orientation of the diffractive features in the gratings and grating portions 10, 21a, 21b, 21c, 22a, 22b, 22c, 30, 210, 221, 222, and 230.

In particular, the diffractive features of the output grating 30 may be substantially parallel to the diffractive features of the out-coupling grating 230. The output grating 30 may also have substantially the same grating period as the out-coupling grating 230. Consequently, the output grating 30 and the out-coupling grating 230 may constitute together a single grating 30. A common portion CPR of the output grating 30 and the out-coupling grating 230 may simultaneously contribute to the illuminating beams B11, B12 as well as to the plurality of beams B2 corresponding to the displayed virtual image.

The imaging unit 400 may be arranged to monitor the eye E1 through a portion of the substrate 7 which does not comprise diffractive features. Such an unobstructed portion may reside e.g. between the grating portions 21a and 21b.

Figure 16A:
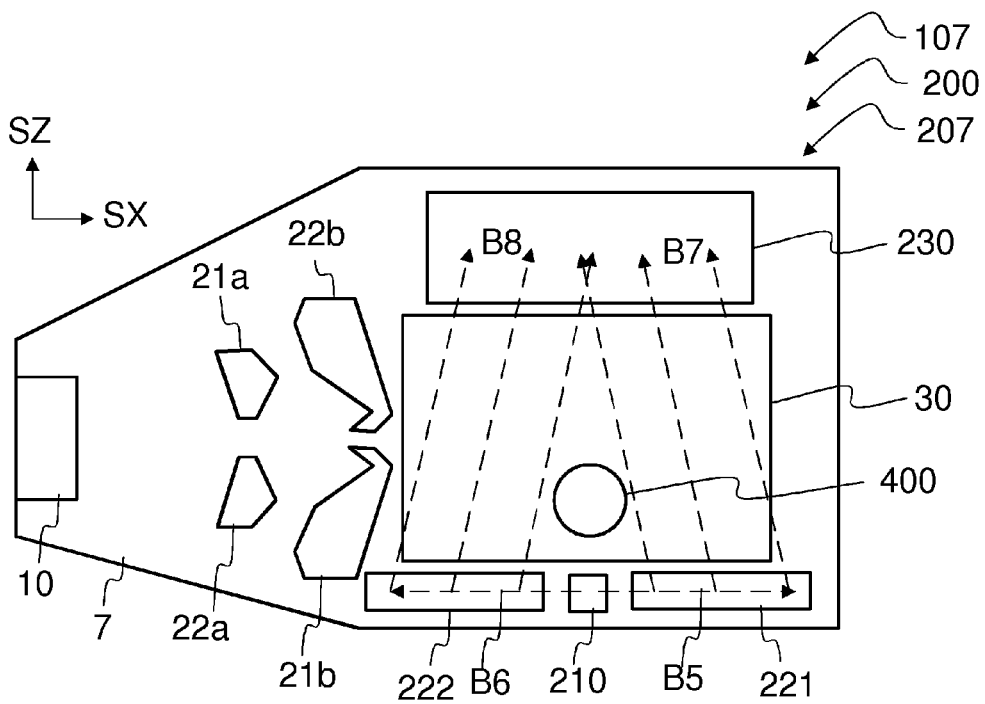
FIG. 16a shows, in a top view, a diffractive beam expander for providing two collimated illuminating light beams.
Figure 16B:
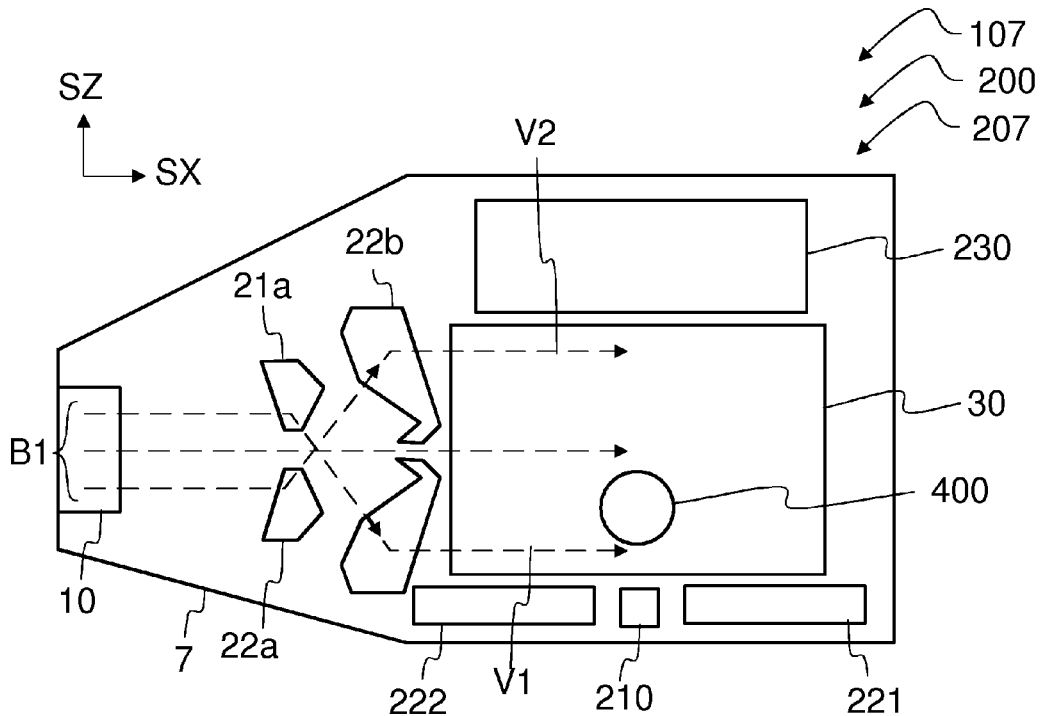
FIG. 16b shows, in a top view, a diffractive beam expander for displaying virtual images.
Figure 16C:
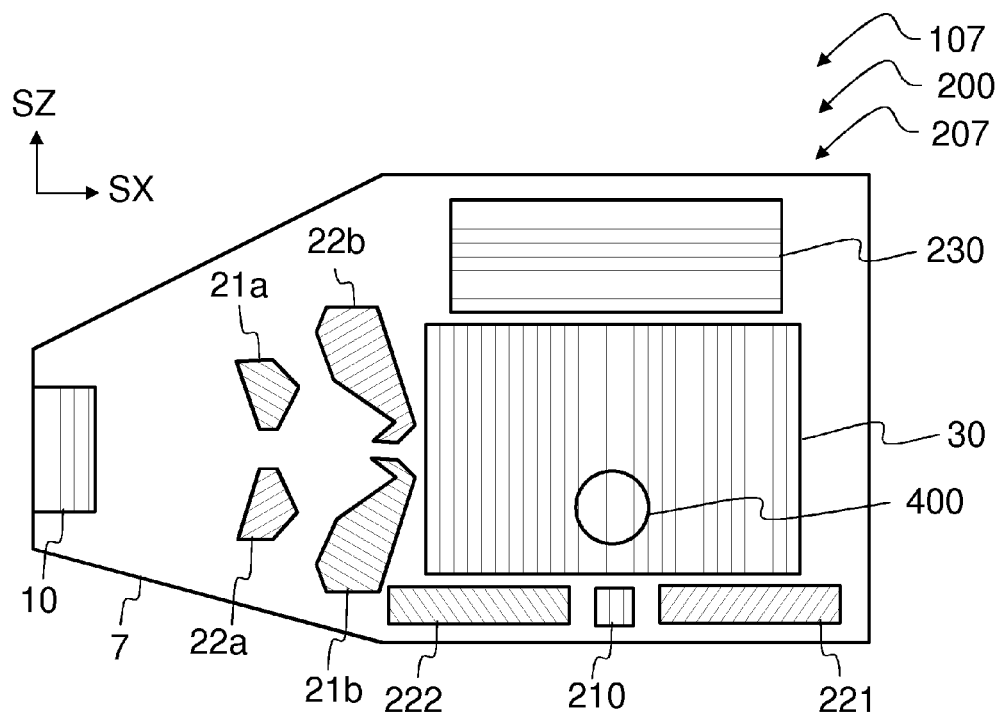
FIG. 16c shows, in a top view, a substrate comprising a first diffractive beam expander for providing two collimated illuminating light beams and a second diffractive beam expander for displaying virtual images.

FIGS. 16a, 16b and 16c show another way to implement the gratings and the grating portions 10, 21a, 21b, 22a, 22b, 30, 210, 221, 222, 230 on the same substrate 7. The hatching in FIG. 16c shows the orientation of the diffractive features in the gratings and grating portions 10, 21a, 21b, 21c, 22a, 22b, 22c, 30, 210, 221, 222, and 230. In particular, the diffractive features of the output grating 30 may be substantially perpendicular to the diffractive features of the out-coupling grating 230. Consequently, the output grating 30 couples a minimum amount of illuminating light out of the substrate 7 although the internal beams B7 and B8 may impinge on the output grating 30 several times before reaching the actual output grating 230. Light beams, in particular infrared beams, which would illuminate the eye E1 from undesired directions can be substantially avoided.

The output grating 30 may at least partly transparent to infrared light. The imaging unit 400 may be arranged to monitor the eye e.g. through the output grating 30.

Figure 17:
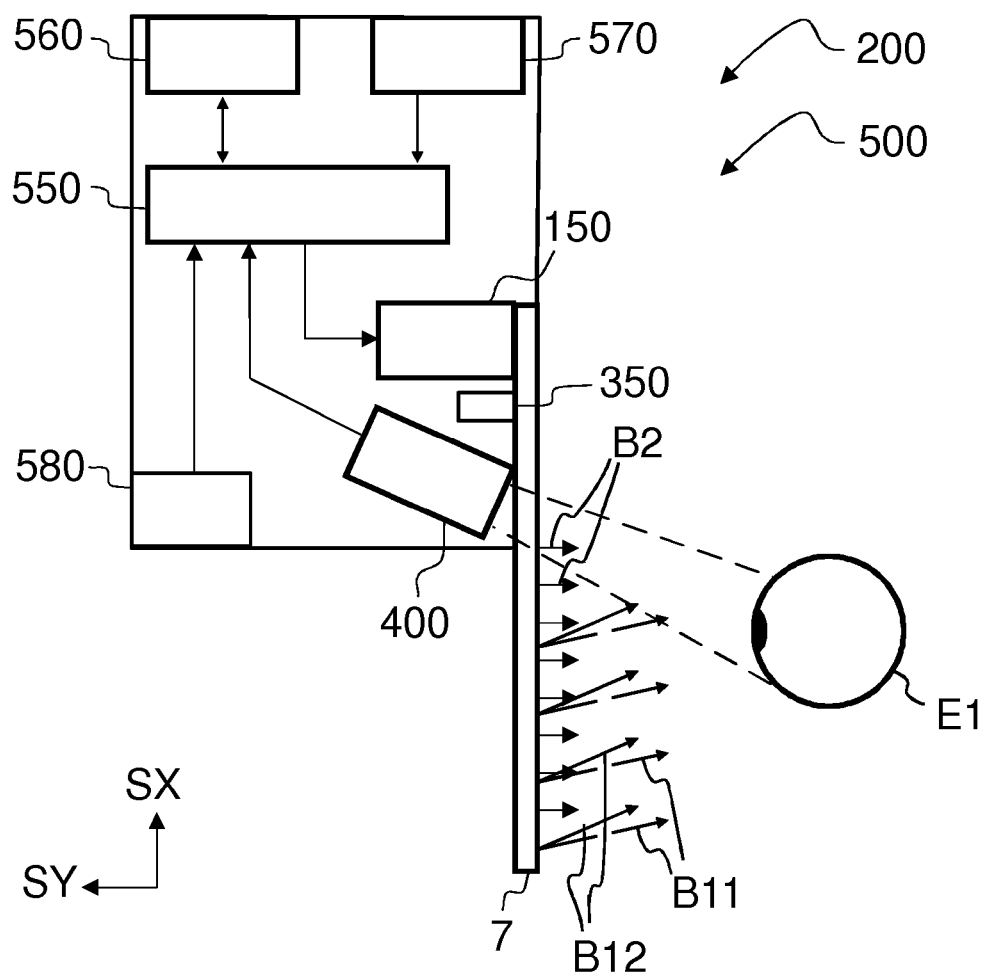
FIG. 17 shows an eye tracking device.

Referring to FIG. 17, an eye tracker device 200 may comprise an imaging unit 400 to acquire an image of the eye E1, a light source 350 to provide a first substantially collimated light beam B0, a first diffractive beam expander 207 to expand the light of said first light beam B0 and to provide at least two enlarged substantially collimated illuminating beams B11, B12. The eye tracker device 200 may comprise a data processing unit 550 to determine the gaze direction GZD on the basis of the image 401 acquired by the imaging unit 400. The eye tracker device 200 may comprise a command interface 570 and a communications unit 560.

The command interface 570 may be a push-button device, joystick or keyboard, which allows a user to send commands to the device 700. The command interface 570 may also be a voice command device or a gesture recognition device. The communications unit 560 may be an interface module for communicating with a computer or mobile device. The communications unit 560 may also be an optical or radio frequency transmitter/receiver, which allows communication via internet or radio network.

The eye tracking device 200 may comprise a position sensor 580 to determine the position of the device 200 with respect to at least one external reference. The external reference may be e.g. a real object or an image displayed on a screen. The position sensor 580 may be e.g. a camera. The position sensor may also be an inertial position sensor comprising one or more gyroscopes and/or accelerometers.

A virtual display device 500 may comprise an optical engine 150 and a further diffractive beam expander 107. The first diffractive beam expander 207 for tracking the gaze direction and the second diffractive beam expander 107 for displaying virtual images may be implemented on the same substrate 7.

The eye tracking device 200 or the virtual display device 500 may be a compact, portable and lightweight device.

The second diffractive beam expander 107 may be arranged to expand the exit pupil of the optical engine 150 such as an expander disclosed in the patent application US 2006/0126182.

The second diffractive beam expander 107 may be arranged to expand the exit pupil of the optical engine 150 such as an expander disclosed in the patent application PCT/FI2007/050322.

The second diffractive beam expander 107 may be arranged to expand the exit pupil of the optical engine 150 such as an expander disclosed in the patent application PCT/FI2006/050590.

Figure 18:
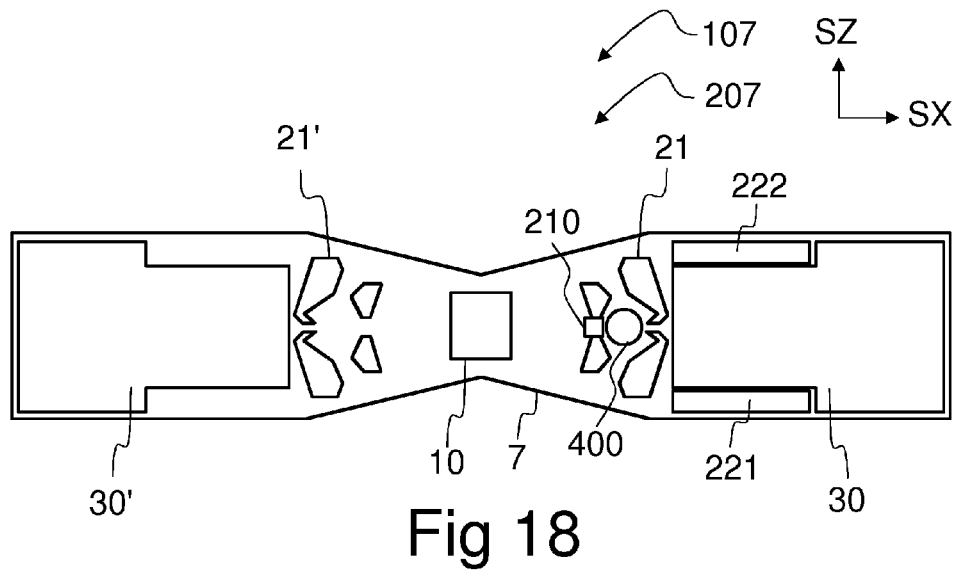
FIG. 18 shows a bi-ocular diffractive beam expander.

Referring to FIG. 18, the same substrate 7 may comprise gratings or grating areas 10, 21, 21', 30, 30', 210, 221, 222, 230 to implement a bi-ocular beam expander 107 suitable for displaying virtual images to both eyes of a viewer and a bi-ocular beam expander 207 for providing the illuminating beams B11, B12 in order to track the gaze direction of at least one eye of said viewer.

The bi-ocular beam expander 107 may be used to implement a virtual display device 500 shown in FIG. 19. The output beams B2 provided by the output gratings 30, 30' to the eyes E1, E2 of a viewer provide for the viewer an impression of a virtual image 1002 displayed at an infinite distance from the viewer. The virtual image 1002 may be e.g. a star pattern as shown in FIG. 19, corresponding to a real image 605 generated by a micro-display 170 (FIG. 10b). The virtual image 1002 may be e.g. graphics and/or text.

The virtual display device 500 may further comprise the eye tracer unit 200 to monitor the gaze direction of the eye E1.

The display device of FIG. 19 may further comprise earpieces 589 which may be positioned on the ears of the viewer in order to facilitate positioning of the virtual display device 500 in front of the eyes E1, E2 of the viewer. The display device 500 may also be attached to a headgear, e.g. to a helmet.

Figure 20:
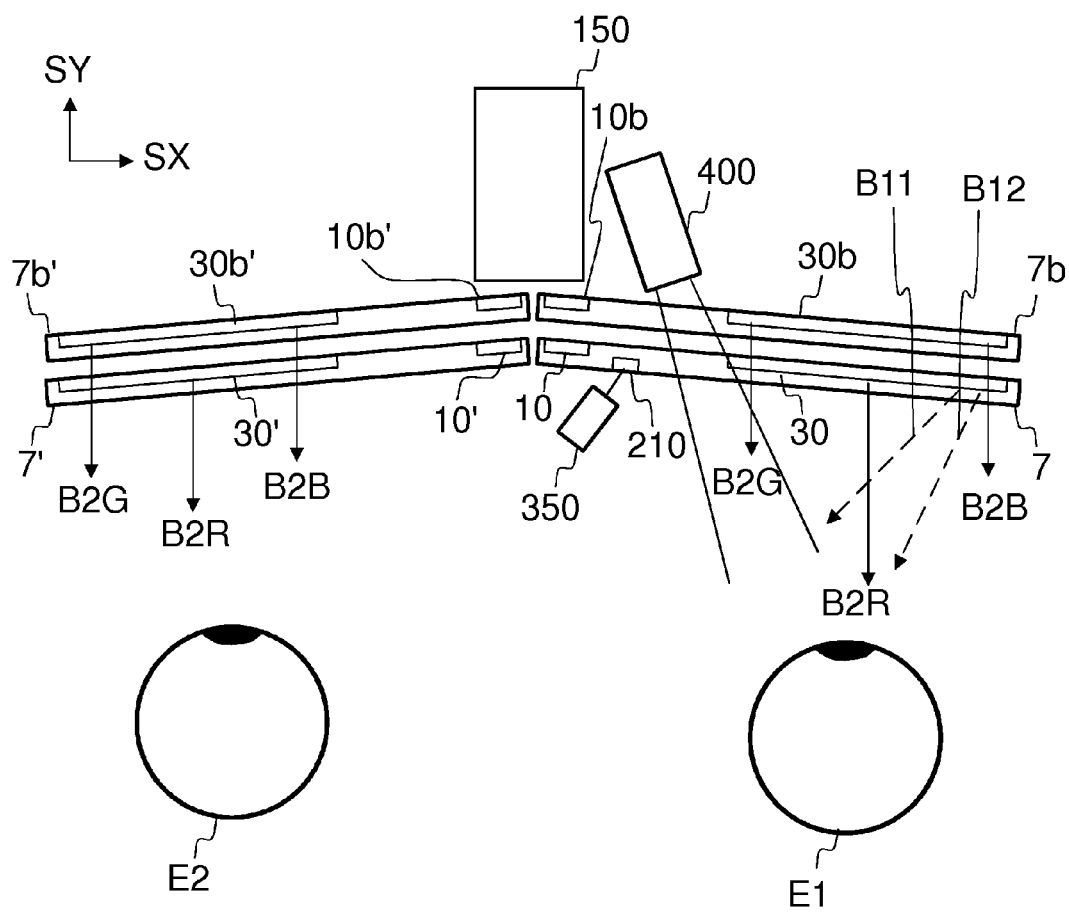
FIG. 20 shows a bi-ocular virtual display device comprising an eye tracer unit.

Referring to FIG. 20, the virtual display device 500 may comprise stacked beam expanders 107 in order to display color images. A first diffractive beam expander 107 implemented on a first substrate 7 may be arranged to display red components B2R of a virtual image. A second diffractive beam expander 107 implemented on a second substrate 7b may be arranged to display green B2G and blue B2B components of the virtual image through the first beam expander. A third diffractive beam expander 107 implemented on a third substrate 7' may be arranged to display red components B2R of a virtual image to the left eye of a viewer. A fourth diffractive beam expander 107 implemented on a fourth substrate 7b' may be arranged to display green B2G and blue B2B components of the virtual image through the third beam expander. Each of the beam expanders 107 may have its own input grating 10, 10', 10', 10b' and output grating 30, 30b, 30', 30b'. A fifth beam expander 207 may be implemented on the first substrate 7 for providing the illuminating beams B11, B12. The light source 350 may also be on the same side of the substrate 7 as the monitored eye E1.

The use of separate substrates for the left eye E2 and the right eye E1 allows more space for the nose of the viewer and a better weight balance than a bi-ocular beam expander 107, 207 implemented on a single straight substrate 7.

Figure 21:
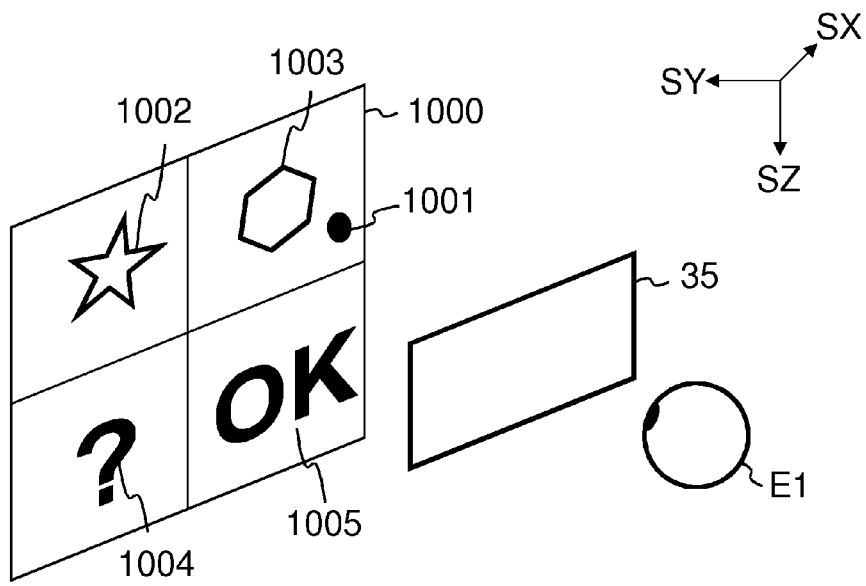
FIG. 21 shows a virtual image viewed through the viewing aperture of a virtual display device.

Referring to FIG. 21, the eye E1 of a viewer may see a displayed virtual image 1000 through the output aperture 35 of the virtual display 100, 500. The virtual image 1000 may comprise displayed objects 1002, 1003, 1004, 1005, for example a star 1002, a hexagon 1003, a symbol "OK" 1005 and a question mark "?" 1004.

The objects or locations of the virtual image 1000 are advantageously associated with gaze directions. Thus, when the eye E1 is looking at an object or location decided by the viewer, it can be determined on the basis of the gaze direction which object or location the eye E1 is looking at. Further, each object or location may be associated with an option, and the viewer may select an option by looking at the respective object or location. The user may confirm the selection e.g. by pushing a button of the command interface 570 (FIG. 17). The user may also confirm the selection by blinking his eye, or by staring at a predetermined object or location for an extended period.

For example, the user may choose between options represented by the object 1002 (star) or the object 1003 (hexagon), by directing his gaze. If the hexagon is chosen, the device 500 may provide visual feedback by blinking after the selection. The user may confirm the selection e.g. by looking at the symbol "OK". Yet, the user may ask for further information by looking at the question mark "?".

The objects 1002, 1003, 1004, 1005 of the virtual image 1000 may be associated with the gaze directions in the software and/or hardware level by e.g. by converting the pixel coordinates of the objects into angular coordinates. The angular coordinates of a displayed object may be compared with the gaze direction to determine whether the user is looking at said object or not.

A visible or invisible cursor 1001 may be adapted to move over the virtual image 1000, following the determined gaze direction of the eye E1. The cursor 1001 helps the user to understand that the tracker device is really following his gaze. In other words, the cursor 1001 provides visual feedback to the user.

The detected gaze direction may be calibrated e.g. by moving a blinking cursor 1001 over the virtual image 1000, and asking the user to look at the cursor 1001. Further, the user may be asked to push the button of the command interface 570 when he is actually looking at the cursor 1001.

Figure 22:
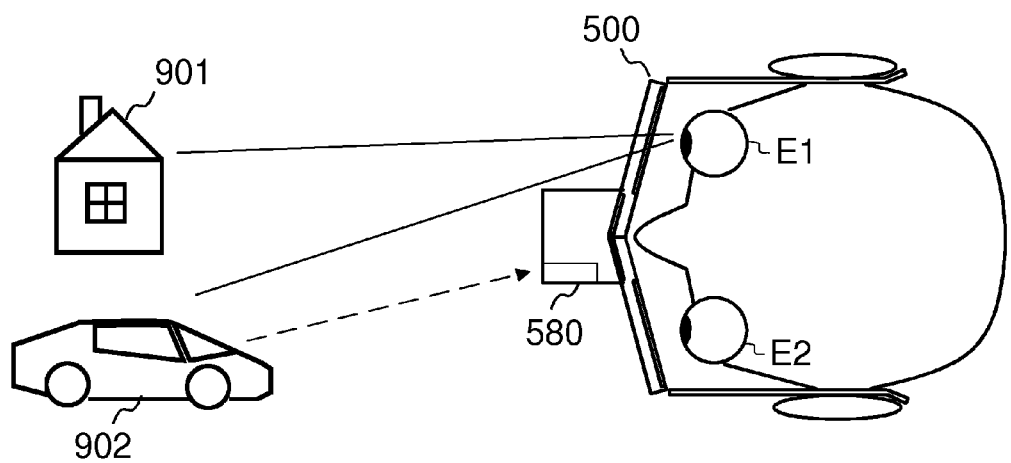
FIG. 22 shows an eye tracking device for determining the gaze direction with respect to external objects.

Referring to FIG. 22, the user may also view physical objects 901 (a house), 902 (a car) through the beam expander 107, 207. The position of the device 500 may be fixed with respect to the objects 901, 902, or the device 500 may comprise a position sensor 580 (FIG. 17) to monitor the position of the device 500 with respect to at least one object 901, 902. Thus, the objects 901, 902, the locations of the objects, and/or the features of a landscape may be associated with the gaze directions. For example, it may be determined whether the user is looking at the house 901 or the car 902. Further, the objects 901, 902 may be associated with options such that an option may be selected by looking at the respective object.

The device 200, 500 may further comprise e.g. a data processing unit, memory and communications unit to provide access to a mobile telephone network, Internet or local area network. The device 200, 500 may be, for example, selected from the following list: a display module connectable to a further device, portable device, device with wireless telecommunicating capabilities, imaging device, mobile phone, gaming device, music recording/playing device (based on e.g. MP3-format), remote control transmitter or receiver, navigation instrument, measuring instrument, target finding device, aiming device, navigation device, personal digital assistant (PDA), communicator, portable internet appliance, handheld computer, accessory to a mobile phone.

For the person skilled in the art, it will be clear that modifications and variations of the devices and the methods according to the present invention are perceivable. The drawings are schematic. The particular embodiments described above with reference to the accompanying drawings are illustrative only and not meant to limit the scope of the invention, which is defined by the appended claims.

The invention claimed is:

1. An apparatus comprising:
a first imaging unit configured to acquire an image of an eye;
a substantially planar waveguiding substrate;
a light source configured to provide a first light beam, said first light beam being substantially collimated;
an in-coupling grating configured to diffract light of said light beam into said substrate and to form a first in-coupled beam and a second in-coupled beam propagating in different directions within said substrate;
a first expanding grating portion configured to provide a first expanded internal beam by diffracting light of said first in-coupled beam;
a second expanding grating portion configured to provide a second expanded internal beam by diffracting light of said second in-coupled beam;
a first out-coupling grating portion configured to form a first substantially collimated illuminating beam by diffracting light of said first internal beam out of said substrate;
a second out-coupling grating portion configured to form a second substantially collimated illuminating beam by diffracting light of said second internal beam out of said substrate, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image; and
a data processing unit configured to determine the gaze direction of the eye with respect to said apparatus based on the position of said first reflection spot in said image, on the position of said second reflection spot in said image, on the position of the pupil and/or iris of the eye in said image and on the directions of the illuminating light beams.

2. The apparatus of claim 1 wherein said first in-coupled beam substantially corresponds to the reflective or transmissive diffraction order −1 and said second in-coupled beam substantially corresponds to the reflective or transmissive diffraction order +1.

3. The apparatus of claim 2 wherein said in-coupling grating is further configured to diffract light of said light beam in the diffraction order 2 or −2 in order to form a third in-coupled beam propagating within said substrate.

4. The apparatus according to claim 1 wherein diffractive features of said first out-coupling grating portion are substantially parallel to diffractive features of said second out-coupling grating portion.

5. The apparatus of claim 4 wherein said first out-coupling grating portion overlaps said second out-coupling grating portion.

6. The apparatus of claim 1 further comprising a position detecting unit to determine the position of said apparatus with respect to at least one external reference.

7. The apparatus of claim 1 being adapted to associate a real object or a location with a gaze direction.

8. The apparatus of claim 1 further comprising an optical engine configured to provide at least one light beam, and a diffractive beam expander to expand said at least one light beam such that a virtual image is visually observable through a viewing aperture of said diffractive beam expander.

9. The apparatus of claim 8 wherein an output grating portion of said diffractive beam expander overlaps said first out-coupling portion.

10. The apparatus of claim 9 wherein an output grating of said diffractive beam expander is substantially perpendicular to said first out-coupling portion.

11. The apparatus of claim 8 being adapted to associate a virtual object with a gaze direction.

12. A method comprising:
acquiring an image of an eye by using a first imaging unit;
providing a substantially collimated first light beam by using a light source;
diffracting light of said first light beam by using an in-coupling grating in order to form a first in-coupled beam and a second in-coupled beam propagating in different directions within a substantially planar waveguiding substrate;
diffracting light of said first in-coupled beam by a first expanding grating portion to provide a first expanded internal beam propagating within said substrate;
diffracting light of said second in-coupled beam by a second expanding grating portion to provide a second expanded internal beam propagating within said substrate;
diffracting light of said first expanded internal beam by a first out-coupling grating portion out of said substrate to form a first substantially collimated illuminating beam;
diffracting light of said second expanded internal beam out of said substrate to form a second substantially collimated illuminating beam, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image; and
determining the gaze direction of the eye based on the position of said first reflection spot in said image, on the position of said second reflection spot in said image, on the position of the pupil and/or iris of the eye in said image and on the directions of the illuminating light beams.

13. The method of claim 12 wherein diffractive features of said first out-coupling grating portion are substantially parallel to diffractive features of said second out-coupling grating portion.

14. The method of claim 13 wherein said first out-coupling grating portion overlaps said second out-coupling grating portion.

15. The method according to claim 12 further comprising:
providing at least one light beam by an using optical engine; and
displaying a virtual image by expanding said at least one light beam by using a diffractive beam expander, said virtual image being observable through a viewing aperture of said diffractive beam expander.

16. The method of claim 15 wherein an output grating of said diffractive beam expander is substantially perpendicular to said first out-coupling portion.

17. A portable apparatus comprising:
a first imaging unit to acquire an image of an eye;
a substantially planar waveguiding substrate;
a light source configured to provide a first light beam, said first light beam being substantially collimated;
an in-coupling grating configured to diffract light of said light beam into said substrate and to form a first in-coupled beam and a second in-coupled beam propagating in different directions within said substrate;
a first expanding grating portion configured to provide a first expanded internal beam by diffracting light of said first in-coupled beam;
a second expanding grating portion configured to provide a second expanded internal beam by diffracting light of said second in-coupled beam;
a first out-coupling grating portion configured to form a first substantially collimated illuminating beam by diffracting light of said first internal beam out of said substrate;
a second out-coupling grating portion configured to form a second substantially collimated illuminating beam by diffracting light of said second internal beam out of said substrate, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image;
a data processing unit configured to determine the gaze direction of the eye with respect to said apparatus based on the position of said first reflection spot in said image, on the position of said second reflection spot in said image, on the position of the pupil and/or iris of the eye in said image and on the directions of the illuminating light beams;
an optical engine configured to provide at least one light beam; and
a diffractive beam expander configured to expand said at least one light beam such that a virtual image is visually observable through a viewing aperture of said diffractive beam expander.

18. The apparatus of claim 17 wherein an output grating of said diffractive beam expander is substantially perpendicular to said first out-coupling portion.

19. An apparatus comprising:
a first imaging means for acquiring an image of said eye;
a substantially planar waveguiding substrate;
a light source means for providing a first light beam, said first light beam being substantially collimated;
an in-coupling grating for diffracting light of said light beam into said substrate and to form a first in-coupled beam and a second in-coupled beam propagating in different directions within said substrate;
a first expanding grating portion for providing a first expanded internal beam by diffracting light of said first in-coupled beam;
a second expanding grating portion for providing a second expanded internal beam by diffracting light of said second in-coupled beam;
a first out-coupling grating portion for forming a first substantially collimated illuminating beam by diffracting light of said first internal beam out of said substrate;
a second out-coupling grating portion for forming a second substantially collimated illuminating beam by diffracting light of said second internal beam out of said substrate, said illuminating beams having different directions such that said first illuminating beam provides a first reflection spot when light is reflected from the surface of the eye and that said second illuminating beam provides a second reflection spot when light is reflected from the surface of said eye, said reflection spots appearing in said image; and
a data processing means for determining the gaze direction of the eye with respect to said gaze direction determining means based on the position of said first reflection spot in said image, on the position of said second reflection spot in said image, on the position of the pupil and/or iris of the eye in said image, and on the directions of the illuminating light beams.

20. The apparatus of claim 19 further comprising an image forming means for providing at least one light beam, and a diffractive expanding means to expand said at least one light beam such that a virtual image is visually observable through a viewing aperture of said diffractive expanding means.

* * * * *